United States Patent
Wootten et al.

(10) Patent No.: US 11,172,978 B2
(45) Date of Patent: Nov. 16, 2021

(54) METHODS, DEVICES AND SYSTEMS FOR INDUCING COLLAGEN REGENERATION

(71) Applicant: Aesthetics Biomedical, Inc., Phoenix, AZ (US)

(72) Inventors: Shaun Wootten, Tempe, AZ (US); Christopher Mark William Daft, Phoenix, AZ (US)

(73) Assignee: Aesthetics Biomedical, Inc., Phoenix, AZ (US)

( * ) Notice: Subject to any disclaimer, the term of this patent is extended or adjusted under 35 U.S.C. 154(b) by 0 days.

(21) Appl. No.: 17/234,648

(22) Filed: Apr. 19, 2021

(65) Prior Publication Data
US 2021/0236193 A1 Aug. 5, 2021

Related U.S. Application Data

(63) Continuation of application No. PCT/US2019/057400, filed on Oct. 22, 2019.
(Continued)

(51) Int. Cl.
*A61B 18/14* (2006.01)
*A61B 18/00* (2006.01)
*A61B 18/12* (2006.01)

(52) U.S. Cl.
CPC ...... *A61B 18/14* (2013.01); *A61B 2018/0047* (2013.01); *A61B 2018/00589* (2013.01);
(Continued)

(58) Field of Classification Search
CPC . A61B 18/14; A61B 18/1402; A61B 18/1477; A61B 18/1206; A61B 18/04;
(Continued)

(56) References Cited

U.S. PATENT DOCUMENTS 5,581,082 A    12/1996  Hansma et al.
5,755,753 A *   5/1998  Knowlton ............. A61B 18/12
                                                        606/33
(Continued)

FOREIGN PATENT DOCUMENTS

EP         3097881 A1    11/2016
WO    WO 1998/005380 A1   2/1998
(Continued)

OTHER PUBLICATIONS

International Search Report & Written Opinion for PCT/US2019/057400 dated Jan. 10, 2020, which is related to the present application.
(Continued)

*Primary Examiner* — Michael F Peffley
(74) *Attorney, Agent, or Firm* — Knobbe, Martens, Olson & Bear, LLP

(57) ABSTRACT

A microneedling system may reciprocate a plurality of microneedles disposed on a handpiece into the skin of a patient. The microneedles and/or electrode plates may deliver RF energy to the patient for inducing collagen coagulation and regeneration. An interrogative modality such as ultrasound may combined into the microneedling handpiece or used as a separate instrument to interrogate the skin and identify or measure the thicknesses of constituent layers. The data obtained from the interrogative modality may be displayed and can be used to automatically adjust operating parameters of the microneedling device, including the penetration depth of the needles, the pulse duration, and/or the power level of the RF energy to optimize the treatment for the specific patient and/or condition being treated. The microneedling system may recall the skin measurements for distinct sectors of the skin which are expected to have different properties.

20 Claims, 5 Drawing Sheets

Related U.S. Application Data

(60) Provisional application No. 62/749,524, filed on Oct. 23, 2018, provisional application No. 62/840,292, filed on Apr. 29, 2019.

(52) U.S. Cl.
CPC ............ *A61B 2018/00875* (2013.01); *A61B 2018/126* (2013.01); *A61B 2018/1425* (2013.01); *A61B 2018/1467* (2013.01); *A61B 2562/028* (2013.01)

(58) Field of Classification Search
CPC .......... A61B 18/12; A61B 2018/00452; A61B 2018/0047; A61B 2018/0016; A61B 2018/00875; A61B 2018/00702; A61B 2018/143; A61B 2018/00464; A61B 2018/1467; A61B 2018/00458; A61B 2018/1425; A61B 90/02; A61N 1/403
See application file for complete search history.

(56) References Cited

U.S. PATENT DOCUMENTS

| | | | |
|---|---|---|---|
| 6,277,116 B1 | 8/2001 | Utely et al. | |
| 7,393,326 B2 | 7/2008 | Bindefeld | |
| 8,101,740 B2 | 1/2012 | Radu et al. | |
| 9,974,463 B2 | 5/2018 | Rutkove et al. | |
| 2004/0002705 A1 | 1/2004 | Knowlton et al. | |
| 2005/0080466 A1 | 4/2005 | Homer | |
| 2005/0256383 A1 | 11/2005 | Gandjbakhche et al. | |
| 2008/0097557 A1* | 4/2008 | Eggers | A61B 18/082 607/99 |
| 2010/0023003 A1 | 1/2010 | Mulholland | |
| 2010/0081971 A1* | 4/2010 | Allison | G16H 20/40 601/2 |
| 2011/0021924 A1 | 1/2011 | Ethuraman et al. | |
| 2011/0218464 A1* | 9/2011 | Iger | A61B 18/14 601/2 |
| 2011/0221438 A1 | 9/2011 | Goodwill et al. | |
| 2014/0330122 A1 | 11/2014 | Baghani et al. | |
| 2015/0032092 A1* | 1/2015 | Adanny | A61B 18/203 606/9 |
| 2015/0038965 A1* | 2/2015 | Iger | A61B 18/1477 606/49 |
| 2015/0057660 A1 | 2/2015 | Jenkins et al. | |
| 2015/0173619 A1 | 6/2015 | Zvuloni et al. | |
| 2016/0016015 A1 | 1/2016 | Slayton et al. | |
| 2016/0228178 A1 | 8/2016 | Lei | |
| 2017/0266457 A1 | 9/2017 | Eckhouse et al. | |
| 2017/0304641 A1 | 10/2017 | Eisenmann et al. | |
| 2018/0110977 A1 | 4/2018 | Palero et al. | |
| 2018/0126160 A1 | 5/2018 | Hyun et al. | |
| 2019/0009085 A1* | 1/2019 | Iger | A61B 18/18 |

FOREIGN PATENT DOCUMENTS

| | | | |
|---|---|---|---|
| WO | WO 2001/024699 A2 | 4/2001 | |
| WO | WO 2016/0185464 | * 11/2016 | ............ A61N 1/04 |
| WO | WO 2016/185464 A1 | 11/2016 | |

OTHER PUBLICATIONS

Website: https://eudelo.com/2018/08/30/treatments-help-build-collagen/, Dated Aug. 30, 2018, Downloaded Mar. 13, 2019, in 7 pages.
International Preliminary Report on Patentability for PCT/US2019/057400 dated Apr. 27, 2021, which is related to the present application.

* cited by examiner

METHODS, DEVICES AND SYSTEMS FOR INDUCING COLLAGEN REGENERATION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of International Application No. PCT/US2019/057400, filed on Oct. 22, 2019, which claims the benefit of U.S. Provisional Application No. 62/749,524, filed Oct. 23, 2018, and U.S. Provisional Application No. 62/840,292, filed Apr. 29, 2019. Each of the aforementioned applications is incorporated by reference herein in its entirety, and each is hereby expressly made a part of this specification.

FIELD OF THE INVENTION

The disclosure herein relates to skin treatment devices for inducing collagen regeneration.

BACKGROUND

Collagen is the most common and abundant form of protein in the body. It is found in many tissues of the muscles, bones, tendons, blood vessels, the digestive system, and skin. As a person ages, their body produces less collagen. This lack of collagen results in the common signs of aging. Wrinkles, sagging skin that has lost its elasticity, and stiff joints are all signs that the body is producing less collagen. When collagen levels are high, the skin is soft, smooth, and firm. Collagen helps the skin cells renew and repair themselves.

SUMMARY

Disclosed herein is a system for inducing collagen regeneration in the skin of a patient. The system includes a handpiece, a non-invasive probe, a processor, and memory storing instructions for operating the processor. The handpiece has a proximal end and a distal end. The distal end includes an electrode array having at least one electrode for delivering electrical energy to the skin of the patient. The non-invasive probe is configured to delineate and measure the thickness of at least one layer of the skin of the patient. The processor is operatively coupled to the electrode array and operatively coupled to the probe. The processor is configured, in response to a measurement of the probe, to adjust one or more operating parameters of the electrode array selected from the group consisting of a waveform frequency of the electrical energy, an amplitude of the waveform, a duration of the electrical energy deliver, and the depth of penetration into the skin of the at least one electrode. In other embodiments, energy other than electrical energy is delivered, e.g., light energy, sound energy, etc.

The probe may be an ultrasound probe, a near-infrared probe, a confocal laser scanning microscopy probe, an optical coherence tomography probe, a diffuse reflectance spectroscopy probe, a computerized tomography probe, a magnetic resonance imaging probe, an atomic force microscopy probe, a positron emission tomography probe, an ultrasound elastography probe, a photoacoustic imaging probe, a magnetic particle imaging probe, an electrical impedance tomography probe, or a Doppler ultrasonography probe. The electrode array may include a plurality of electrodes. The plurality of electrodes may include electrodes of opposite polarity. One of the polarities may be electrical ground. In some embodiments, the system may include a ground electrode separate from the electrode array and configured to be coupled to the patient. The electrode array may have at least one microneedle electrode configured to be inserted the skin of the patient. The at least one microneedle may be configured to be inserted into the skin at an adjustable penetration depth. The penetration depth may be adjusted in response to the measurement of the probe. The microneedle electrode may be configured to be inserted such that a distal tip of the microneedle electrode reaches the dermis. The microneedle electrode can be insulated or uninsulated. The electrode array may have a surface electrode configured to be pressed into contact with the surface of the skin without puncturing the skin. The surface electrode may be a plate electrode.

The processor may be configured to adjust the waveform frequency in response to the probe measurement. The processor may be configured to adjust the waveform amplitude in response to the probe measurement. The processor may be configured to adjust the pulse duration of the electrical energy in response to the probe measurement. The processor may be configured to adjust a power level of electrode array by adjusting a combination of the waveform amplitude and waveform frequency. The processor may be configured to adjust the one or more operating parameters of the electrode array based in part on an input desired volume of coagulation (damage). The processor may be configured to estimate one or more volumes of coagulation based on the operating parameters and the probe measurement.

The system may include a display operatively coupled to the processor. The display may be configured to depict an image of the skin in which at least one layer of the skin is delineated from another. The processor may be configured to depict the penetration depth of one or more microneedles on the image. The processor may be configured to depict one or more predicted volumes of coagulation on the image. The processor may be configured to depict one or more measurements of the thickness of a layer of the skin on the display. The processor may be configured to aggregate measurements from the probe to determine a representative measurement for a sector of skin.

The processor may be configured to adjust the operating parameters of the electrode array based on a selection of a specific sector of skin which is to be treated. The selectable sectors may comprises the face and/or different sectors of the face. The processor may be configured to delineate the epidermis, dermis, subcutaneous tissue, and muscle.

The system may include a user interface through which a user can adjust the operating parameters and/or input parameters. The memory may store a plurality of user-selectable programs which use different algorithms for adjusting the operating parameters of the electrode array in response to the probe measurement. At least one of the user-selectable programs may be specific to a skin condition to be treated.

The probe may be disposed on the handpiece. The probe may be positioned laterally to the electrode array. The probe may be axially aligned with the electrode array relative to a longitudinal axis extending from the proximal end to the distal end of the handpiece. The probe may be positioned proximally behind the electrode array. The probe may be disposed on an instrument separate from the handpiece. The separate instrument and the handpiece can be operatively coupled to a single housing unit for modulating operation of both the probe and the electrode array.

The electrode array may be detachable from the handpiece. The electrode array may be configured to deliver the electrical energy in one or more confined volumes, e.g., a damage volume or a confined electrocoagulation volumes. In certain embodiments, a "damage volume" can be a volume where the damage is confined to the output of the electrode array and where the damage is caused by electrical energy. The one or more volumes may be defined by a threshold electrical impedance input and/or a threshold temperature. An energy or waveform amplitude or waveform period can be adjusted, e.g., automatically adjusted, based off of the threshold electrical impedance value, wherein the electrical impedance value is obtained by an invasive or non-invasive electrode. The energy or waveform amplitude or waveform period can be adjusted to define a damage or electrocoagulation volume in a selected tissue layer or layers of tissue of the patient. The threshold temperature may be about 55 degrees Celsius. The system may be configured to estimate the size of the one or more electrocoagulation volumes. The size of the one or more electrocoagulation volumes may be estimated based on one or more of the power level, frequency, pulse duration, and/or total treatment time. The system may be configured to automatically adjust the depth of the one or more electrocoagulation volumes based on the estimated size of the one or more electrocoagulation volumes and based on a measured thickness of the at least one layer of skin as measured by the non-invasive probe. The depth of the one or more electrocoagulation volumes may be adjusted by automatically adjusting the penetration depth of the at least one electrode. The depth of the one or more coagulation volumes may be adjusted in order to confine the one or more coagulation volumes to a selected layer of skin. The selected layer may be the dermis. The system may be configured to minimize the penetration depth of the at least one electrode. The system may be configured to maximize the size of the one or more coagulation volumes for a selected depth while preventing the one or more coagulation volumes from extending into one or more select layers of skin.

In another aspect of the present disclosure, disclosed herein is a system for inducing collagen regeneration in the skin of a patient. The system includes a handpiece, a non-invasive probe, and a processor. The handpiece has a proximal end and a distal end. The distal end has an electrode array having bipolar electrodes for producing a confined volume of electrocoagulation at a select depth beneath a surface of the skin of the patient. The non-invasive probe is configured to delineate and measure the thickness of at least one layer of the skin of the patient. The processor is operatively coupled to the electrode array and operatively coupled to the probe. The processor is configured to adjust the depth of the volume of electrocoagulation beneath the surface of the skin according to an algorithm based in part upon a measurement of the non-invasive probe.

In another aspect, a system is provided for inducing collagen regeneration in the skin of a patient, the system comprising: a handpiece having a proximal end and a distal end, the distal end comprising an electrode array comprising bipolar electrodes for producing a confined volume of electrocoagulation at a select depth beneath a surface of the skin of the patient; a non-invasive probe configured to delineate and measure the thickness of at least one layer of the skin of the patient; a non-invasive or invasive electrode configured to obtain electrical impedance values of at least one layer of the skin of the patient; and a processor operatively coupled to the electrode array and operatively coupled to the probe, wherein the processor is configured to adjust the depth of the volume of electrocoagulation beneath the surface of the skin according to an algorithm based in part upon a measurement of the non-invasive probe.

In another aspect of the present disclosure, disclosed herein is a method of inducing collagen regeneration in the skin of a patient. The method comprises measuring the thickness of at least one layer of the skin of the patient with a non-invasive probe; contacting the skin of the patient and delivering electrical energy to the skin of the patient via an electrode array; and adjusting via a processor, based on a measurement of the probe, one or more operating parameters of the electrode array. The operating parameters are selected from the group consisting of: a waveform frequency of the electrical energy, an amplitude of the waveform, a duration of the electrical energy deliver, and the depth of penetration into the skin of the at least one electrode. Penetration depth can range from resting on the skin (a depth of 0 mm) to a depth of, e.g., 1 mm, 2 mm, 3 mm, or more below the surface of the skin.

The probe may be an ultrasound probe. The probe may be a near-infrared probe. The electrode array may include a plurality of electrodes. The plurality of electrodes may include electrodes of opposite polarity. One of the polarities may be electrical ground. The method may further comprise applying a ground electrode separate from the electrode array to the patient. The electrode array may include at least one microneedle electrode configured to be inserted the skin of the patient. The at least one microneedle may be configured to be inserted into the skin at an adjustable penetration depth. The method may further comprise adjusting the penetration depth in response to the measurement of the probe. The microneedle electrode may be configured to be inserted such that a distal tip of the microneedle electrode reaches the dermis. The microneedle electrode may be insulated or uninsulated. The electrode array may include a surface electrode configured to be pressed into contact with the surface of the skin without puncturing the skin. The surface electrode may be a plate electrode.

The method may comprise adjusting, via the processor, the waveform frequency in response to the probe measurement. The method may comprise adjusting, via the processor, the waveform amplitude in response to the probe measurement. The method may comprise adjusting, via the processor, the pulse duration of the electrical energy in response to the probe measurement. The method may comprise adjusting, via the processor, a power level of the electrode array by adjusting a combination of the waveform amplitude and waveform frequency. The method may comprise adjusting, via the processor, the one or more operating parameters of the electrode array based in part on an input desired volume of coagulation. The method may comprise estimating, via the processor, one or more volumes of coagulation based on the operating parameters and the probe measurement.

The method may comprise displaying an image of the skin in which at least one layer of the skin is delineated from another. The method may comprise displaying the penetration depth of one or more microneedles on the image. The method may comprise displaying one or more predicted volumes of coagulation on the image. The method may comprise displaying one or more measurements of the thickness of a layer of the skin.

The method may comprise aggregating measurements from the probe, via the processor, to determine a representative measurement for a sector of skin. The method may comprise adjusting the operating parameters of the electrode array based on a selection of a specific sector of skin which is to be treated. The selectable sectors may comprise the face and/or different sectors of the face. The method may comprise delineating the epidermis, dermis, and subcutaneous tissue of the skin of the patient, via the processor.

The method may comprise inputting operating parameters into a user interface. The method may comprise selecting one of a plurality of user-selectable programs stored on a memory to adjust the operating parameters of the electrode array in response to the probe measurement. At least one of the user-selectable programs may be specific to a skin condition to be treated.

The probe may be disposed on the handpiece. The probe may be positioned laterally to the electrode array. The probe may be axially aligned with the electrode array relative to a longitudinal axis extending from the proximal end to the distal end of the handpiece. The probe may be positioned proximally behind the electrode array. The probe may be disposed on an instrument separate from the handpiece. The separate instrument and the handpiece may be operatively coupled to a single housing unit for modulating operation of both the probe and the electrode array.

The electrode array may be detachable from the handpiece. The electrode array may be configured to deliver the electrical energy in one or more confined electrocoagulation volumes. The one or more electrocoagulation volumes may be defined by a threshold temperature. The threshold temperature may be about 55 degrees Celsius. The method may further comprise estimating the size of the one or more electrocoagulation volumes. The estimating may be performed based on one or more of the power level, frequency, pulse duration, and/or total treatment time. The method may further comprise automatically adjusting the depth of the one or more electrocoagulation volumes based on the estimated size of the one or more electrocoagulation volumes and based on a measured thickness of the at least one layer of skin as measured by the non-invasive probe. The depth of the one or more electrocoagulation volumes may be adjusted by automatically adjusting the penetration depth of the at least one electrode. The depth of the one or more coagulation volumes may be adjusted in order to confine the one or more coagulation volumes to a selected layer of skin. The selected layer may be the dermis. The method may comprise minimizing the penetration depth of the at least one electrode. The method may comprise maximizing the size of the one or more coagulation volumes for a selected depth while preventing the one or more coagulation volumes from extending into one or more select layers of skin.

In another aspect of the present disclosure, disclosed herein is a method for inducing collagen regeneration in the skin of a patient. The method comprises measuring the thickness of at least one layer of the skin of the patient with a non-invasive probe; producing a confined volume of electrocoagulation at a select depth beneath a surface of the skin of the patient; and adjusting via a processor the depth of the volume of electrocoagulation beneath the surface of the skin according to an algorithm based in part upon a measurement of the non-invasive probe.

BRIEF DESCRIPTION OF THE DRAWINGS

Features of the present disclosure will become more fully apparent from the following description and appended claims, taken in conjunction with the accompanying drawings. It will be understood that these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description" one will understand how illustrated features serve to explain certain principles of the present disclosure.

FIG. 1A depicts a handpiece comprising both the microneedle array and the ultrasound probe. FIG. 1B depicts a handpiece comprising the microneedle array an a separate handpiece comprising the ultrasound probe, each operatively coupled to the same housing unit.

FIG. 3A depicts a face divided into separate regions, which may each have different tissue characteristics and may benefit from microneedling procedures performed under different operating parameters. FIG. 3B depicts a display showing an ultrasound image of interrogated tissue and relative information determined from the ultrasound as well as interface features for modulating the microneedling operating parameters. FIG. 3C depicts the image shown on the display of FIG. 3B with the addition of predicted volumes of coagulation from RF treatment through the microneedles and an image of the distal tip of the microneedling handpiece overlaid.

DETAILED DESCRIPTION

Figure 1A:
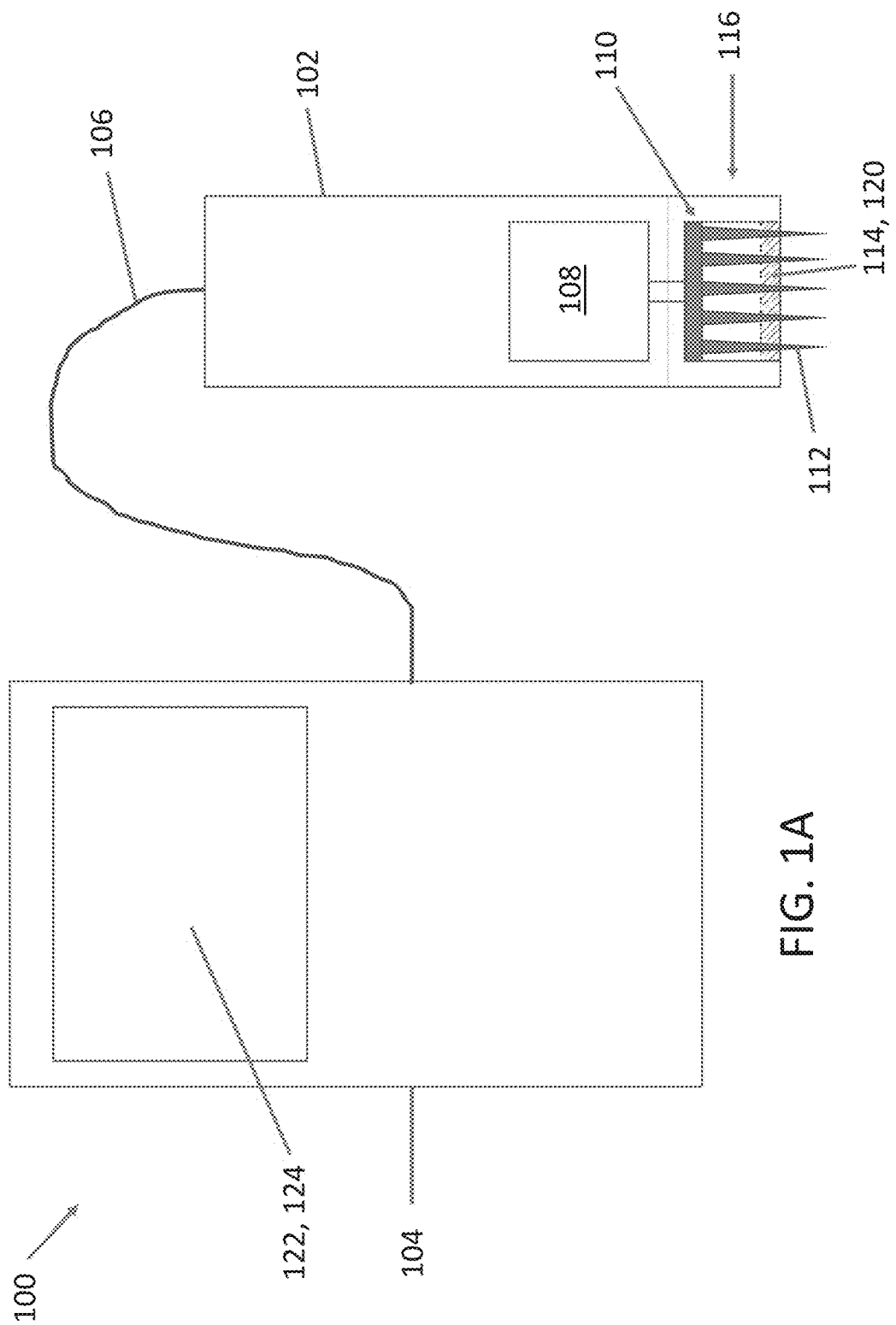
FIGS. 1A-1B schematically depict examples of a microneedling system comprising a microneedle array and an ultrasound probe operatively coupled to a housing unit.
Figure 1B:
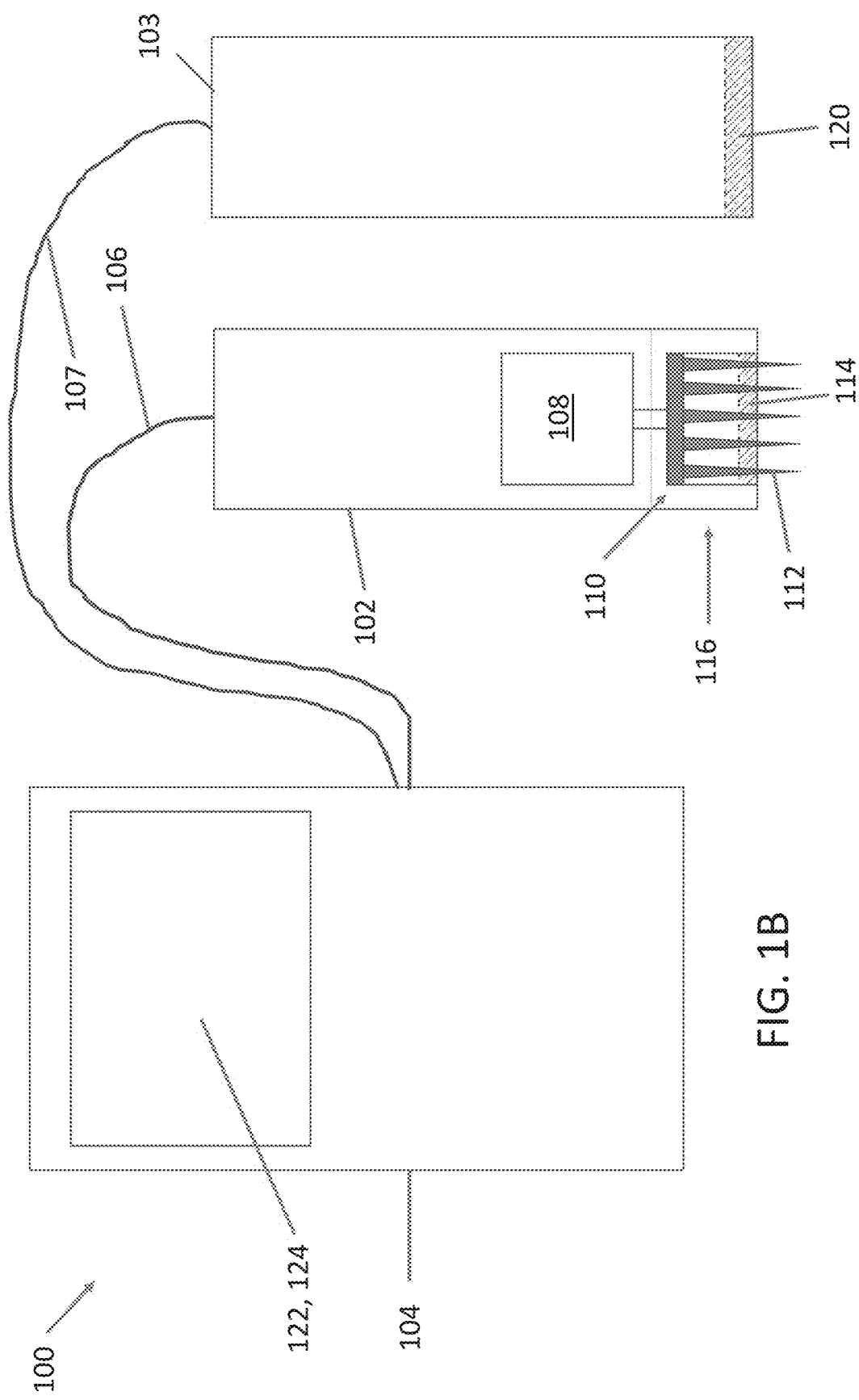

Disclosed herein is a microneedling system configured for providing a therapeutic treatment to a patient (e.g., a human patient). The microneedling system may be used to provide a cosmetic treatment, such as collagen induction therapy. FIGS. 1A-1B schematically depict examples of a microneedling system 100. The microneedling system 100 may include a handpiece 102 configured to be held by the operator for applying the treatment to the patient's skin. In some embodiments, the handpiece 102 is configured to be connected to a housing unit 104, which may be configured to control at least some operations of the handpiece 102 by a transmission line 106. The transmission line 106 may transfer power from the housing unit 104 to the handpiece 102. The transmission line 106 may communicate data or electrical signals between the housing unit 104 and the handpiece 102 (e.g., from the housing unit 104 to the handpiece 102 and/or from the handpiece 102 to the housing unit 104). In some embodiments, there may be no transmission line 106. The handpiece 102 may be battery-powered by a battery contained within the handpiece 102. In some embodiments, data and signals may be wirelessly communicated between the handpiece 102 and a housing unit 104 or a remote processor by any means known in the art.

The handpiece 102 may include a proximal end and a distal end. The handpiece 102 may comprise a generally elongate body extending between the proximal end and the distal end. The elongate body may be configured for grasping and handling by an operator. The transmission line 106 may extend from a proximal end of the handpiece 102. The handpiece 102 may comprise a microneedle array 110 for applying the microneedling treatment to the patient. The term "array" as used herein is a broad term, and is to be given its ordinary and customary meaning to a person of ordinary skill in the art (and is not to be limited to a special or customized meaning), and refers without limitation to an assembly of two or more components, e.g., for a microneedle array, two or more microneedles in an assembly. An array can be, but is not required to be, an ordered assembly of components, e.g., each component spaced from another by a same distance, or a series of components assembled in a line. In certain embodiments, the array can comprise at least one component, e.g., an electrode array comprising at least one electrode. The microneedle array 110 may comprise one or more microneedles 112 (e.g., 1, 2, 3, 4, 5, 6, 6, 8, 9, 10, 20, 30, 50, 60, 70, 80, 90, 100, or more than 100) extending from or configured to be extendable from the distal end of the handpiece 102. The microneedles 112 may be configured to penetrate the skin of the patient; however, in certain embodiments the microneedles can be adapted to rest upon the skin without piercing the epiderdermis. The microneedles 112 may be used to induce collagen generation in the treated skin of the patient. The microneedles 112 may be arranged in a generally parallel fashion to each other such that the microneedles 112 are configured to be applied to penetrate the skin in a direction normal to the surface of the skin (e.g., when the elongate body of the handpiece 102 is held normal to the surface of the skin). The microneedles 112 may be arranged across a two-dimensional area of the microneedle array 110. In some embodiments, the microneedles 112 be arranged in rows and/or columns. The microneedles 112 may be uniformly spaced from each other in a regular pattern. The microneedles 112 may be configured to extend a uniform distance from the distal end of the elongate body such that the microneedles 112 may extend a uniform penetration depth into the skin of the patient. In some embodiments, one or more of the microneedles 112 may extend further (e.g., deeper) than one or more of the other microneedles 112. In some embodiments, one or more of the microneedles 112 may be configured to extend an adjustable depth into the skin of the patient when the distal end of the elongate body is held near or against the surface of the skin. For instance, in some implementations, the depth may be set between approximately 0.5 mm and 5 mm or between 0.5 mm and 3.5 mm. In some embodiments, the depth may be adjustable by 0.1, 0.2, 0.3, 0.4, 0.5, or 1 mm increments. In some embodiments, one or more of the microneedles 112 may have a diameter of no more than about 0.05 mm, 0.1 mm, 0.2 mm, 0.3 mm, 0.4 mm, or 0.5 mm. In some embodiments, the microneedles 112 may have a generally uniform diameter (e.g., circular) over the majority of the length of the needle, ending distally in a pointed tip. In some embodiments, the diameter may gradually taper over a distal portion of the length of the needle. In some embodiments, one or more of the microneedles 112 may be gold-plated.

The handpiece 102 may comprise a motor 108 (e.g., a micro-memory motor) for driving the microneedle array 110 in an oscillatory motion configured to puncture the skin of the patient. The motor 108 may drive each of the microneedles 112 simultaneously in a linearly reciprocating motion. In some embodiments, the microneedles 112 may be driven in in a reciprocating motion in a temporally staggered fashion, such as in a linear (e.g., left-to-right) wave motion. The distal end of the handpiece 102 may be configured to be held against the skin of the patient prior actuating the microneedle array 110 such that the microneedles 112 are inserted a known depth into the skin when the motor 108 reciprocates the microneedle array 110. In some embodiments, the handpiece 102 may comprise a needle plate 114 through which the one or more microneedles 112 of the microneedle array 110 may extend during the skin puncturing motion. The needle plate 114 may comprise an aperture for each microneedle 112 through which the microneedle 112 may pass. The tip of the microneedle 112 may be positioned proximally behind or within the needle plate 114 such that the tips of the microneedles 112 are configured not to contact the skin in a resting state (e.g., prior to and/or after the microneedles 112 are reciprocated into the skin of the patient). The needle plate 114 may form a distal surface of the handpiece 102 such that the needle plate 114 may be placed into substantial contact with the skin during the treatment and the microneedles 112 may puncture and pass through the skin as they are extended distally beyond the needle plate 114 by the motor 108. In some embodiments, there may be no needle plate 114. In some embodiments, the handpiece 102 may comprise an opening at its distal end through which the tips of all the microneedles 112 may extend. The perimeter or rim of the opening may act as a contact surface which contacts the skin during treatment and positions the microneedles 112 a known distance from the skin prior to reciprocation. In some embodiments, the handpiece 102 may comprise an opening and a needle plate 114. The needle plate 114 may be positioned within the opening. The needle plate 114 may be positioned substantially flush with the edge of the opening or proximally positioned behind the opening. In some embodiments, the transmission line 106 may provide power to the motor 108 for driving the reciprocating motion. In some embodiments, the distal end of the handpiece 102 may comprise a detachable tip 116. The detachable tip 116 may enclose the microneedle array 110. The detachable tip 116 may be configured to detachably engage one or more pistons or other mechanical linkages extending from the motor 108. The detachable tip 116 may be configured for single-patient use (e.g., disposable) such that the detachable tip 116 can be replaced for different patients. The detachable tip 116 may be provided presterilized in sealed packaging.

The microneedle array 110 may be configured to apply radiofrequency (RF) energy to the treated skin of the patient via an electric field. The RF energy may be configured to heat confined volumes of the patient's skin (e.g., the dermis) to denature the proteins (e.g., the collagen) in the skin and induce a wound healing response that involves new collagen formation. Without being limited by theory, the RF energy may heat the tissue through the Joule effect, and the temperature achieved may depend in part on the resistivity of the heated tissue. The temperature reached by the application of RF energy may be configured to induce irreversible collagen coagulation, which may be ideal for promoting collagen regeneration. One or more of the microneedles 112 may be configured to serve as electrodes for delivering the RF energy to the skin. In some embodiments, all of the microneedles 112 may serve as electrodes. The puncture wound created by the microneedles 112 may induce wound healing and/or collagen regeneration. In some implementations, the effect between the puncturing and the thermal damage may be synergistic. In some embodiments, the microneedles 112 may be configured as monopolar electrodes in which all of the microneedle electrodes are configured as the same polarity (e.g., positive or negative) and the electrical charge delivered by the handpiece 102 is dissipated into the skin. The current may travel to a remote ground electrode not part of the handpiece 102. In some embodiments, the microneedles 112 may be configured as bipolar electrodes in which one or more of the microneedles 112 are configured as electrodes of a first polarity and one or more of the microneedles 112 are configured as electrodes of a second polarity, opposite the first polarity. Current supplied by the handpiece 102 may travel from the first polarity electrodes to the second polarity electrodes through the skin. The current may be an alternating current alternating at a frequency within the radiofrequency range such that the electrodes alternate between functioning as anodes and cathodes. Any other suitable frequency may also be employed. Bipolar stimulation of the skin may provide more confined and predictable volumes of treatment than monopolar stimulation. The electrode microneedles 112 may be either insulated or non-insulated. Non-insulated microneedles 112 may deliver the electrical current over the entire length of the microneedle 112. Insulated microneedles 112, may comprise a non-conductive covering over a proximal portion of the microneedle 112 which confines the delivery of the electrical current to the tip of the microneedle 112 (e.g., the distal most 0.1, 0.2, 0.3, 0.4, 0.5, 0.6, 0.7, 0.8, 0.8, or 1.0 mm). The collagen inductive effects may be greatest at the tip of the microneedles 112.

The microneedling system 100 may be configured to automatically deliver the RF energy during discrete time intervals. The time intervals may correspond to a period coinciding with the full insertion of each individual microneedle 112 through which the energy is delivered. In embodiments, in which the microneedles 112 are not all inserted simultaneously, corresponding electrodes (e.g., paired electrodes) through which an electric field is established may be configured to be inserted simultaneously or to at least be fully inserted during the duration of the RF energy pulse. In some embodiments, the electric current may be applied over one or more pulses of RF energy (e.g., 1, 2, 3, 4, 5, or more than 5 pulses) during each cycle of microneedle 112 insertion. In some embodiments, the pulse may be at least about 10, 50, 100, 200, 300, 400, 500, 600, 800, 900, or 1000 milliseconds in duration. The motor 108 may be configured to pause the reciprocating movement for a period of time equal to or greater than the duration of the one or more pulses, such that the microneedles 112 are not moving while they act as electrodes to deliver RF energy. In some embodiments, the total power delivered to the microneedle array 110 may be at least about 5, 10, 20, 30, 40, 50, 60, 70, 80, 90, or 100 W.

In some embodiments, one or more or all of the microneedles 112 may be substituted with probe electrodes (e.g., with flat or rounded distal tips) or conductive plates that are not configured to penetrate the skin. The electrodes may be placed into contact with the surface of the skin and deliver RF energy from the surface of the skin (e.g., through the epidermal layer). For instance, in some embodiments, the microneedle array 110 may comprise a single electrode plate for monopolar delivery of RF energy to the patient's skin. The system 100 may operate substantially the same as described elsewhere herein, excluding the modulation of penetration depth of the microneedle 112 electrodes. The RF energy will necessarily travel through superficial layers of skin (e.g., the epidermis) in passing through a surface electrode. Cooling treatments may be applied to the surface of the skin, as is known in the art, to avoid or mitigate damage to the superficial layers of the skin.

In embodiments comprising bipolar electrodes, the RF energy may be substantially confined to discrete fields between one or more electrodes of a first polarity and one or more electrodes of a second polarity, opposite the first polarity. The confined fields may form volumes of coagulation in which the tissue temperature within the volume is sufficiently raised to a degree sufficient to induce collagen coagulation, as described elsewhere herein. In some implementations, collagen may begin to denature at about 40-48 degrees Celsius. Collagen may coagulate at about 55-70 degrees Celsius. Higher temperatures may require shorter durations of heating to induce coagulation or permanent denaturation. The area or volume of raised temperature (e.g., coagulation volume) may expand over the duration of heating. The area or volume of raised temperature may expand more rapidly at higher temperatures. The microneedle array 110 may produce one or more volumes of coagulation. Each volume may be shaped by the electric field between proximate microneedles 112 of opposite polarity. In some embodiments, each volume may be generally spherical or ellipsoid. In some implementations, one or more of the volumes of coagulation may merge together forming a combined volume of coagulation in which the constituent volumes are indistinguishable. In some implementations, one or more of the volumes of coagulation may touch or overlap, such that each of the constituent volumes remains distinguishable from the others. In some implementations, one or more of the volumes of coagulation may remain sufficiently isolated such that there is no overlap or contact between the volumes. For a given arrangement of microneedles 112 of a microneedle assay 110, maintaining the volume of one or more volumes of coagulation below threshold levels may keep the volumes separate and distinct such that they are separated by regions of tissue in which collagen is not coagulated and the tissue remains relatively unwounded. In some implementations, this allows delivering the RF energy in a fractionated manner, in which wounded volumes of tissue are surrounded by healthy tissue. Fractionating the RF energy may advantageously promote the wound-healing response. The unaffected skin may promote more rapid wound healing of adjacent coagulation volumes. The minimization in the total coagulation volume may result in less pain to the patient and/or a more rapid recovery time.

In some embodiments, the handpiece 102 may comprise one or more sources of laser light for treating the patient's skin. For instance, the handpiece 102 may comprise one or more LEDs (laser emitting diodes) configured to produce light of specific wavelengths for providing therapeutic treatment to the skin. For example, a blue LED light may be used to disrupt bacterial growth. A red LED light may be used to stimulate collagen production. The source of light may be positioned laterally to the microneedle array 110 and/or may be positioned proximally behind the microneedle array 110. In some embodiments, components of the handpiece 102 positioned distally to the light source, such as possibly the microneedle array 110 and/or the needle plate 114 may be translucent or at least partially translucent to the wavelengths of light transmitted by the light source such that light may pass distally through the distal end of the handpiece to the patient's skin. In some implementations photonic stimulation may be provided through a separate instrument or handpiece to supplement the microneedling treatment.

In some implementations, the ideal penetration depth of the microneedles 112 may depend on the thickness of the skin, the desired effects of the treatment, and/or the particular area of the body where the skin is being treated. For instance, an ideal penetration depth for treatments designed to tighten the skin via collagen induction may be one which reaches the dermis layer of the skin. In some implementations, the lower (deeper) layers of the dermis may be the optimal target depth for the tips of the microneedles 112. An ideal penetration depth for treatments designed to treat superficial scarring of the skin (e.g., acne scarring) may be one which does not surpass the epidermal layers of the skin or which only reaches very superficial layers of the dermis. In some implementations, the subcutaneous layers may be avoided. Avoiding the subcutaneous layers may avoid excessive damage, bleeding, and/or pain to the patient. The thickness of the skin, particularly the thickness of the epidermis layers may vary from patient-to-patient and/or depending on the location of the skin on the patient (e.g., the forehead, cheeks, neck, stomach, etc.). For instance, the epidermis may be much thinner on the neck of a patient than on the cheeks of a patient. Also, the dermis may become thinner with age or exposure to other environmental factors, such as UV radiation. The amount of fat deposits between patients may vary and effect the thicknesses of one or more layers of skin. For instance, a patient's Body Mass Index (BMI) may be correlated to skin thickness. Accordingly, the optimal microneedle 112 penetration depth may depend on the thickness of the skin of a precise treatment area for a particular patient as well as on the specific results to be achieved.

The microneedling system 100 may employ an interrogative modality such as ultrasound to locally measure and/or differentiate the layers of skin of one or more treatment areas of interest on a patient. In some implementations, ultrasound may be used to stimulate collagen formation to supplement the microneedling treatment. The microneedling system 100 may comprise an ultrasound probe 120 comprising a transducer as is generally known in the art for medical imaging (sonography). The ultrasound transducer may comprise one or more piezoelectric crystals configured to vibrate in response to an electrical input signal to produce ultrasound waves that may be used to interrogate the skin of the patient. The one or more piezoelectric crystals may be configured to receive and vibrate in response to reflected ultrasound waves to produce an electric output signal. The piezoelectric crystal mays comprise any material generally known in the art, such as but not limited to, lead zirconate titanate (PZT), lead titanate (PT), lead metaniobate (PMN), bismuth titanate (BT), polyvinylidene fluoride (PVDF), polyvinyledenedifluoride-tetrafluoroethylene copolymer (p(VDF-TrFE)), and/or composites thereof. A processor may be configured to interpret the output signal (e.g., the time-dependent voltage response and/or current response) to deduce physiological information about the interrogated tissue and/or to construct an image of the interrogated tissue. A signal generator may produce the input signal and may be connected to the ultrasound probe 120 by an input wire or cable. In some embodiments, the housing unit 104 may house the signal generator. The processor may be operatively coupled to the ultrasound probe 120 by an output wire or cable. The input and output wires may be separate or combined into a single ultrasound line. The ultrasound line may be the same as transmission line 106 or may be a separate line.

In some embodiments, the ultrasound probe 120 may be incorporated into the handpiece 102, as shown in FIG. 1A. The ultrasound probe 120 may be positioned at or near a distal end of the handpiece 102. In some embodiments, the ultrasound probe 120 may be arranged to be substantially laterally offset from the microneedle array 110. The field of view of the ultrasound may be offset from the prospective treatment area of the microneedle array 110 at any point in time, and may or may not overlap the prospective treatment area of the microneedle array 110 at any instant. In some embodiments, the ultrasound probe 120 may be arranged in substantial axial alignment with the microneedle array 110, such that the field of view of the ultrasound probe 120 is substantially the same as, encompasses, or is substantially centered within the prospective treatment area of the microneedle array 110 at any point in time. The ultrasound probe 120 may be positioned proximally behind the proximal ends of the microneedles 112 and possibly other components of the handpiece 102. One or more of the components positioned distally in front of the ultrasound probe 120 may comprise materials configured to minimize reflection of the ultrasound waves and/or the processor may be configured to account for the distortion of any handpiece 102 components positioned within the field of view of the ultrasound probe 120.

In some embodiments, the ultrasound probe 120 may be enclosed within or may function as the needle plate 114. One or more piezoelectric crystals may be arranged between and/or around the apertures configured to allow the microneedles 112 to pass through or may be arranged such that they form the apertures. When the microneedles 112 are proximally retracted beyond the distal face of the needle plate 114, the ultrasound probe 120 can image the field of view without obstruction by the microneedles 112. The processor may be configured to account for any gaps created by the needle apertures. The ultrasound probe 120 may be operable when the microneedles are partially or fully extended beyond the distal face of the needle plate 114. The processor may be configured to account for the distortion in the image by the portions of any microneedles 112 within the field of view of the ultrasound probe 120. In some embodiments, the transducer may be arranged as a substantially linear array of piezoelectric crystals. The length of the array may be generally equal to or less than a lateral dimension of the distal end of the handpiece 102, such as the lateral dimension of the microneedle array 110. The width of the array may be substantially less than the length of the array and/or substantially less than a transverse lateral dimension of the distal end of the handpiece 102. The linear array be positioned between two rows or two columns of microneedles. In some embodiments, the piezoelectric crystals of the array may be arranged along a substantially flat plane. The ultrasound probe 120 may be configured to produce substantially parallel ultrasound waves from each of the piezoelectric crystals. In some embodiments, the piezoelectric crystals of the array may be arranged along a substantially curved surface. The ultrasound probe 120 may be configured to produce substantially divergent ultrasound waves from the plurality of crystals. In some embodiments, the ultrasound probe 120 may comprise a phased array transducer configured to provide a wide field of view from a relatively small transducer footprint. The piezoelectric crystals of the transducer array may be fired simultaneously, sequentially, and/or in any other suitable temporal fashion. The ultrasound probe 120 may be configured to interrogate or scan a substantially narrow slice of skin at any moment of time. In some embodiments, the slice of tissue interrogated may be substantially less thick than the width of the prospective treatment area of the microneedle array 110.

In some embodiments in which the handpiece 102 comprises a detachable tip 116, the ultrasound probe 120 may be configured to be detachable from the elongate body of the handpiece 102 with the microneedle array 110 but separable from the disposable microneedle array 110 such that the ultrasound probe 120 may be reattached to another detachable tip 116 for repeated use. In some embodiments, the ultrasound probe 120 may be non-detachable from an elongate body of the handpiece 102. In some embodiments, the ultrasound probe 120 may be positioned within the elongate body proximal to the detachable tip 116. In some embodiments, the ultrasound probe 120 may extend axially along a lateral side of the detachable tip 116 or may extend into an interior of the detachable tip 116 such that the detachable tip 116 is removable from around the ultrasound probe 120.

In some embodiments, the ultrasound probe 120 may be carried by handpiece 103 which is separate and distinct from handpiece 102 carrying the microneedle array 110, as shown in FIG. 1B. For instance, the ultrasound probe 120 may be the same as or similar to commercially available ultrasound probes for sonography.

In some embodiments, the ultrasound probe 120 may be operably coupled to the housing unit 104 of the microneedling system 100. The ultrasound probe 120 may be connected to the housing unit 104 by a transmission line 107. The transmission line 107 may transfer power from the housing unit 104 to the ultrasound probe 120. The transmission line 107 may communicate data or electrical signals between the housing unit 104 and the ultrasound probe 120 (e.g., from the housing unit 104 to the ultrasound probe 120 and/or from the ultrasound probe 120 to the housing unit 104). In some embodiments, there may be no transmission line 107. The ultrasound probe 120 may be battery-powered by a battery contained within the ultrasound probe 120. In some embodiments, data and signals may be wirelessly communicated between the ultrasound probe 120 and a housing unit 104 or a remote processor by any means known in the art. In other embodiments, the ultrasound system may be a stand-alone apparatus, but may be operably coupled to the microneedling system 100 such as through a general purpose computer, such that data may be shared with the microneedling system 100.

In some embodiments, the ultrasound probe 120 may be substituted with or supplemented with another interrogative modality (e.g., an imaging modality). For instance, the ultrasound probe 120 may be substituted with or supplemented with an infrared probe. The infrared probe may emit and detect radiation within the infrared spectrum (e.g., near-infrared), as is known in the art, and may analyze the information to identify and/or determine the thickness of one or more layers of skin. The microneedling system 100 may use information detected from infrared detection or other interrogative modalities in the same or a substantially similar manner to that described elsewhere herein with respect to ultrasound. For instance, the microneedling system may automatically adjust operating parameters based on quantitative and/or qualitative assessments of the skin using one or more interrogative modalities, such as infrared scanning.

The microneedling system 100 may comprise an interface 122 configured for interaction with an operator to operate the handpiece 102. The interface 122 may include one or more user inputs for incrementing, decrementing, or otherwise altering one or more operating variables of the microneedling system 100. The interface 122 may comprise one or more power and/or actuation switches for turning power to the system 100 and/or the handpiece 102 off/on and/or for initiating, pausing, stopping, restarting a function, such as motor oscillation, application of RF energy, laser treatment, and/or ultrasound imaging. In some embodiments, in addition to or alternative to the control via the interface 122, one or more of these functions may be controlled by interface mechanism disposed on the handpiece 102 and/or on an implement at least somewhat remote from the housing unit 104, such as a foot switch operably coupled to the housing unit 104 or a keyboard or mouse operably coupled to a processor in communication with the housing unit 104 and/or the handpiece 102. The interface 122 may include buttons, switches, knobs, a keyboard, a mouse, and/or a touchscreen interface. The touchscreen interface may include widgets for receiving input from an operator. The microneedling system 100 may comprise a display 124 (e.g., a monitor screen) for displaying information to an operator. In some embodiments, the display 124 may function as a touchscreen interface forming at least part of the interface 122, as depicted in FIGS. 1A-1B. The display 124 may be configured to display a graphical user interface (GUI) through which an operator can control the functioning of the microneedling system 100.

The microneedling system 100 may comprise one or more processors and/or memory. The processors and/or memory may be distributed between the housing unit 104, the handpiece 102, the ultrasound handpiece 103 (if a separate component), and one or more computing systems operably coupled to the housing unit 104 in any suitable combination or arrangement. The microneedling system 100 may comprise software for operating the system, including but not limited to controlling the motor 108, controlling the power supplied to the RF electrodes, controlling the signal generator generating ultrasound waves, and/or interpreting the output signals of the ultrasound transducer 120. The software may be stored on memory within any one or more of the components of the system and/or stored on a remote server. The one or more processors may be in communication (e.g., wireless communication) with the servers for accessing the software. The memory may store one or more programs, which may comprise preselected operating parameters and/or treatment protocols. In some embodiments, the programs may be stored on remote servers. The housing unit 104 may comprise a power source (e.g., a battery) and/or may be configured to couple to an external power source (e.g., a standard wall AC outlet).

In certain embodiments, the safety and efficacy of the micro-needling treatments described herein can be further enhanced by a system providing real-time information on the progress of the treatment. This information can be in the form of an indication of the volume which has been treated by each micro-needle. The parameters of the treatment, including but not limited to the position of the needle and the RF frequency and power delivered through it, can then be altered based upon the real-time feedback about the volume which has been treated.

In embodiments where progress of the treatment is to be determined, the system can incorporate modifications of the imaging apparatus and software, such that volume data (three dimensional) instead of slice data (two dimensional) is obtained. To accomplish this, the transducer can include a grid of elements, rather than a line of elements. To monitor treatment progression, the ultrasonically scanned volume encompasses the treatment volume. This means that the transducer elements are dispersed among the needles. Signal processing techniques are employed which sense and quantify the extent to which the tissue has been changed during the course of the treatment.

Figure 2:
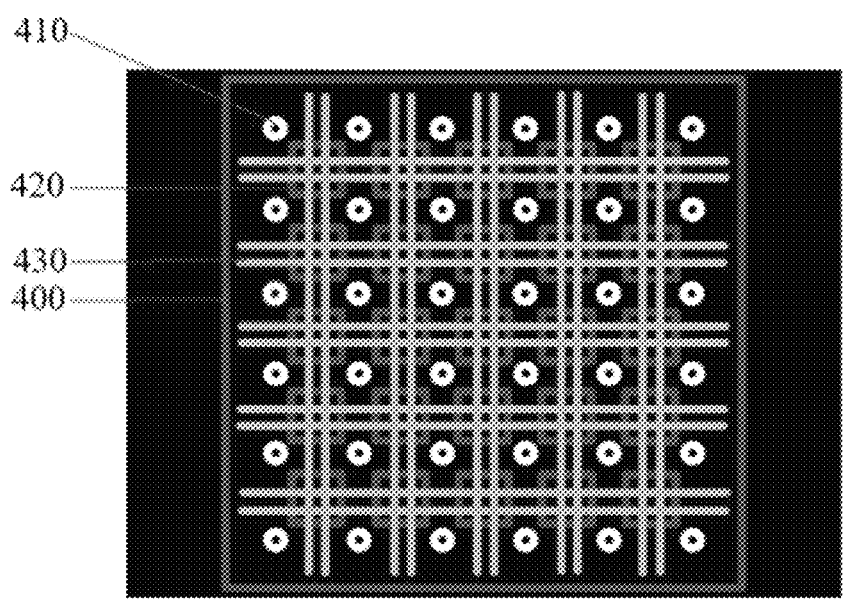
FIG. 2 schematically depicts an exemplary handpiece comprising an array of micro-needles and the ultrasound areas. It has a 6×6 array of needles in a grid spanning a 15×15 mm square area.

In certain embodiments, the micro-needles are interspersed with the imaging array such that treatment volume data can be obtained as treatment progresses. In contrast to certain other embodiments, in these embodiments there is no separate handpiece and non-invasive probe. Instead, the handpiece and non-invasive probe are combined. An illustration of a configuration is depicted in FIG. 2. In this embodiment, The micro-needles have a typical diameter of 0.3 mm, and are typically spaced by 2.5 mm, which permits the spaces between the micro-needles 410 to be adapted to incorporate ultrasound elements. In FIG. 2, the sizes of the micro-needles 410 and the ultrasound areas 420 in the array on the handpiece 400 are shown schematically. The depicted array has a 6×6 array of micro-needles in a grid spanning a 15×15 mm square area. The number of micro-needles and ultrasound areas can be adjusted as desired, e.g., 2×2, 3×3, 4×4, 5×5, 6×6, 7×7, 8×8, 9×9, 10×10, 11×11, 12×12, 6×12, 4×10, etc. The spacing can also be adjusted, e.g., 1.5 mm or less to 3.5 mm or more, or 2 mm to 3 mm, or 2.25 mm to 2.75 mm, although a spacing of approximately 2.5 mm is generally suitable to therapeutic uses as described herein.

In the diagram of FIG. 2, the white circles are the micro-needles 410 which have a radius of 0.5 mm to allow for clearance. The micro-needles 410 are spaced by 2.5 mm. The green square represents the exterior of the handpiece 400. The dark blue squares are the ultrasonically sensitive regions 420. The light blue lines represent (without detail) the electrical connections 430 between the ultrasound integrated circuits (Ics) and the circuitry elsewhere in the handpiece 400. The ultrasound ICs are squares with a size of 1.5 mm in length/width.

The ultrasound ICs can be Micro-Electro-Mechanical Systems (MEMS) transducers which are controlled from the edges of the handpiece. Alternatively (for higher performance) the MEMS transducers can be bonded to mixed-signal ICs which perform beam formation, such that there are fewer wires exiting the MEMS+IC combinations, also referred to as "tiles", than there are acoustic elements. The number of acoustic elements within the ultrasonic tiles depends upon the frequency in use. For example, with a 15 MHz center frequency, the elements can have a dimension of around 100 μm, so a tile can comprise 225 elements (15×15). At a 30 MHz center frequency, there are can be 900 elements.

One advantage of using MEMS transducers such as piezoelectric MicroMachined Ultrasound Transducers (pMUTs) or capacitive MicroMachined Ultrasound Transducers (cMUTs) over bulk transducers is that the small elements employed for high frequency imaging are straightforward to produce, whereas a bulk transducer is defined by a saw with a kerf width of at least 25-35 μm. Making an array transducer with a pitch of 50 μm is not practical with the traditional dice-and-fill techniques used with bulk Lead Zirconate Titanate (PZT). Another advantage is that connecting a MEMS device to the IC is much easier than with a bulk transducer. Such devices and integrated circuits are commercially available.

After the data have been collected from the ultrasound tiles, the data are processed in order to determine how far the treatment has progressed and the dimensions of the treated area. Several Quantitative UltraSound (QUS) signal processing techniques can be used to provide this information. Examples of parameters which can be extracted fall into two broad categories: 1) spectral biomarkers, which are computed from short-time Fourier transforms of the ultrasound data; and 2) backscatter coefficient biomarkers, which are obtained directly from the time domain data. Examples of spectral biomarkers include backscattered power, scatterer concentration, and scatterer size. Examples of backscatter coefficient biomarkers include the average acoustic concentration (AAC) and the average scatterer dimension (ASD). Cell death and malignancy can both alter these QUS biomarkers. Accordingly, the formation of collagen may have a marked effect on them. Additionally, signal processing may reveal the temperature of the tissue during the treatment for additional monitoring of the process.

Figure 3:
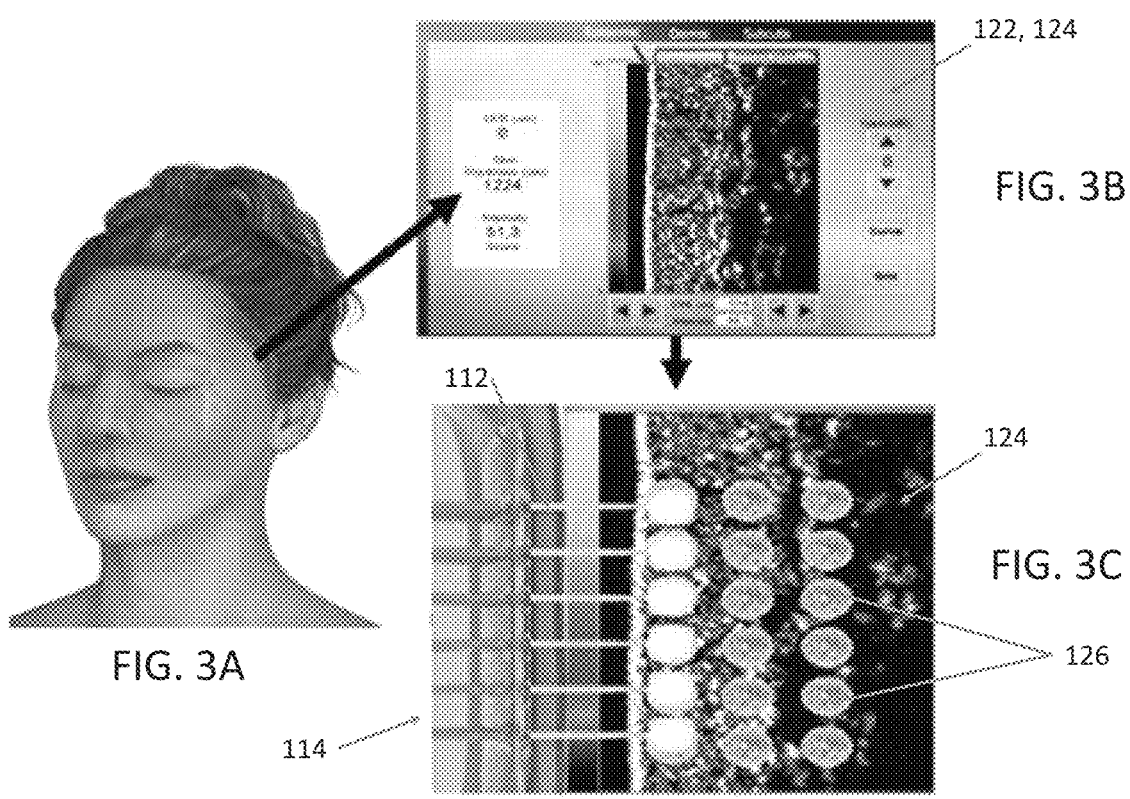
FIGS. 3A-3C schematically depicts an example using ultrasound data in combination with the microneedling system.

FIGS. 3A-3C illustrate an example of using how the microneedling system 100 may use data obtained from the ultrasound probe 120 (or another interrogative modality) to modulate the microneedling procedure. FIG. 3A depicts the face of a patient where portions of the facial skin are divided into discrete regions (e.g., forehead, cheeks, periorbital, temple, zygomatic, chin, nasal, etc.). Some regions may be divided into sub-regions. In some embodiments, the microneedling system 100 may use programs designed for treatment of a specific area of the body (e.g., a specific region of the face). The microneedling treatment may also be applied to other areas of the body, including but not limited to the neck, décolleté, stomach, hands, arms, legs, torso, etc. Each of these body areas may have distinct skin profiles (e.g., different proportions of layers and thicknesses, different levels of sensitivity, etc.). Some or all of these regions may be further divided into sub-regions having different skin profiles. In some embodiments, a representative image of the body, face, or other body area may be displayed on the display 124. Target areas for treatment may be visually indicated and/or selectable through the display 124. In some embodiments, the display 124 is configured to display an image of the skin constructed from the ultrasound probe 120, as shown in FIG. 3B. The image may be a 2-dimensional image of the skin along a plane substantially normal to the surface of the skin. In some embodiments, the depth of penetration of the ultrasound probe 120 may be configured to capture the epidermis, the dermis, and at least a portion of the subcutaneous layer of the tissue, as shown in FIG. 3B. In some embodiments, the depth of penetration may be configured to capture the epidermis and at least a portion of the dermis. The image may distinguish areas of the interrogated tissue based on echogenicity or the relative ability of the tissue to reflect the ultrasound waves supplied by the ultrasound probe 120. Hyperechoic tissue or tissue that is more prone to reflect the ultrasound waves may show up more brightly than hypoechoic tissue or tissue that is less prone to reflect the ultrasound waves. The image may be supplemented with a scale bar that depicts the scale of relative echogenicity in the image. The image and scale bar may be displayed in grey scale or in color. In some embodiments, the image may not be derived directly from the ultrasound data but may simply be a delineation skin layers based on the thicknesses of a plurality of layers as determined by the processor.

In some implementations, the epidermis, dermis, and subcutaneous layers may be visually discernible from each other. The echogenicity of each layer may be influenced by the most abundant molecular components of each, including keratin in the epidermis, collagen in the dermis, and fat or adipose tissue in the subcutaneous layer. In some implementations, the epidermis may appear as a hyperechoic line, the dermis as a less bright hyperechoic band, and the subcutaneous layer as a hypoechoic region. In some images, the hyperechoic line corresponding to the epidermis may not correspond to the epidermis itself but may be generated as a result of reflections from the surface of the skin. In some implementations, one or more of the various sub-layers or other structures within the skin may be discernible. The epidermis which is comprised primarily of keratinocytes may be divided into basal, spinous, granular, and corneous layers in order of increasing superficiality. A basal membrane of macromolecules may connect the basal layer to the collagen fibers of the dermis. A thin anechoic artifact band known as a subepidermal low-echogenic band (SLEB) may appear between the epidermis and the dermis, and may be particularly prominent in older patients and/or patients with UV-damaged skin. The dermis may be divided into a superficial papillary dermis (approximately 20% of the dermis) and an underlying reticular dermis (approximately 80% of the dermis). The majority of the dermis may be connective tissue comprising collagen and elastin fibers. The dermis may also comprise blood vessels. The extracellular matrix fibers of the papillary dermis may be thinner and less orderly arranged than the extracellular matrix fibers of the reticular dermis which are thicker and arranged regularly. Collagen fibers may produce hyperechoic reflections relative to the surrounding extracellular matrix. An upper and lower layer of the dermis may be discernible in which the upper layer is hypoechoic relative to the lower layer, resulting potentially from weaker reflections of the ultrasound waves by the collagen. However, the division between the upper and lower visible layers of the dermis may not perfectly correspond to the papillary dermis and the reticular dermis. In some embodiments, the processor may use algorithms to distinguish one or more of the layers or sublayers based on the echogenicity and relative depth of the layers. The divisions between identified layers may be indicated on the display 124 as shown in FIG. 3B. The processor may be configured to determine thickness measurements for one or more of the layers and may optionally display one or more selective measurements to the operator. In some implementations, the processor may rely on calibration data for determining the thickness and/or identities of various layers of skin.

In some implementations, the ultrasound probe 120 may be moved across the surface of the skin over one or more regions to assess and/or measure the skin layers of the prospective treatment areas. The ultrasound probe 120 may be used with or without ultrasound gel. The ultrasound probe 120 may continually capture different (e.g., adjacent) slices of tissue as the ultrasound probe 120 is moved. The display 122 may display the captured images substantially in real time and/or may update the image in discernable increments of time. In some embodiments, the handpiece 102, handpiece 103, and/or the housing unit 104 may comprise an image capture button that allows the capture of images in moments of time. The captured image may be displayed until a new image is captured and/or until the display is switched back to a real-time or other mode of visualization. The processor may continually analyze the data in real time. The processor may determine the thicknesses of layers in real time. The processor may be configured to compile or aggregate data. For instance, the processor may determine an average or median thickness for each of the identified layers over a particular region of the skin (e.g., where the measurements are not expected to drastically vary). Increased ultrasound scanning over an area of skin may produce more accurate results. The display 122 may depict the real-time measurements and/or aggregate measurements. In some implementations, the processor may determine representative measurements and/or characteristic for each sector to be treated (e.g., cheeks, neck, forehead, etc.).

In some embodiments, the operator may scan a local area and then subsequently perform a microneedling treatment on that local area using the data obtained from the ultrasound probe 120. The operator may continually scan new areas of skin in which the skin characteristics are expected to significantly differ prior to treating that area of skin. In some embodiments, an entire heterogeneous region of the body (e.g., the face) may be scanned with the ultrasound probe 120 prior to initiating the microneedling treatment. The microneedling system 100 may log results for discrete regions of tissue (e.g., the chin, the cheeks, the forehead) such that it can recall the data for that particular region. Subsequently to the scanning process, the operator may select which region he or she is preparing to perform the microneedling treatment on and the display 124 may recall the data from that region, may display a representative image from that region, and/or may update the operating parameters according to an algorithm or preselected program for that region. In some embodiments, a 3-dimensional tracking system may be used with the microneedling system. Detectable fiduciary markers (e.g., optically detectable) may be placed on the patient (e.g., on several points of the face) and the one or more handpieces 102, 103 of the system. A remote detection system (e.g., a camera) may be used to track the 3-dimensional coordinates of the one or more handpieces 102, 103 relative to the target tissue of the patient such that the microneedling system 100 may update the operating parameters in substantially real-time based, based on prior ultrasound scanning with ultrasound probe 120 and on the real-time positioning of the handpiece 102 relative to the patient.

One or more operating parameters may be adjusted based upon the quantitative and/or qualitative assessment of the skin via the ultrasound probe 120. The adjustable operating parameters may be adjusted manually by the operator and/or automatically according to one or more algorithms, which may or may not depend on the selection of a stored treatment program. In some embodiments, one or more of the operating parameters may be set automatically unless manually overridden by the operator. For instance, the penetration depth of the microneedles 112, the frequency of the RF energy, the duration of the RF pulse, the total treatment time (e.g., cumulative duration of pulses over a sector of skin), and/or the power of the RF energy may be modulated. In some implementations, the frequency, pulse duration, total treatment time, and/or the power of the RF energy may be modulated to control the temperature and/or the size (e.g., volume) of the one or more coagulation volumes (via the electric fields) produced by the microneedles 112. Coagulation volumes may be defined, in some implementations, by volumes of skin which reach a certain temperature. One or more processors of the system 100 may employ one or more algorithms to determine or predict the size (e.g., volume) of coagulation based on the aforementioned operating parameters (e.g., frequency, pulse duration, treatment time, and/or power level). In some implementations, the precise coagulation volume may be dependent on the targeted tissue layer (e.g., type of tissue having a particular resistivity) which may optionally be input into the system (e.g., as part of a preprogrammed treatment). Depending on the application, the targeted skin layer, the thickness of the targeted skin layer, and/or the proximity of adjacent skin layers, larger or smaller volumes of coagulation may be desired. The optimal temperatures achieved within the tissue resulting from the electric field applied may also depend on the application and the tissue being treated. Accordingly, the frequency, duration, and/or the power level of the RF energy may be adjusted based on the measurements and/or assessment provided by the ultrasound probe 120.

In some implementations, the operating parameters (e.g., frequency, pulse duration, treatment time, and/or power level) may be selected based on a desired treatment, skin condition, result, and/or other input parameters (e.g., patient age) or be determined by a pre-selected program. The system 100 may be configured to automatically adjust the microneedle 112 penetration depth in response to the delineated skin layers of measured thicknesses and the calculated size of coagulation volumes. The system 100 may be configured to adjust the penetration depth such that the anticipated coagulation volumes are confined to target layers of skin or otherwise located in relatively precise target volumes of skin for any given skin sector. For instance, the system 100 may be configured to minimize the penetration depth of the microneedles 110 while confining the volumes of coagulation to the dermis or other layer or sublayer of skin. In some implementations, the system 100 may adjust the volume of coagulation (via one or more operating parameters) based on a desired penetration depth (e.g., maximize the coagulation volume for a certain depth while confining the coagulation volume to a selected layer of skin). In some embodiments, the electrodes may not be microneedles 110 which physically penetrate the skin of the patient. For instance, the system 100 may comprise bipolar surface electrodes or any other electrode arrangement for stimulating electrocoagulation within the skin, as discussed elsewhere herein. One or more operating parameters may be adjusted to modulate the target depth and/or size (e.g., volume) of the electrocoagulation. The system 100 may comprise algorithms as described elsewhere herein for automatically optimizing the depth and/or size of the electrocoagulation volumes based on the measured thicknesses of skin layers within a target region of skin.

In some embodiments, the power level may be selectable from an arbitrary incremented scale (e.g., 1 to 10, 1 to 5, etc.). The voltage/current and frequency of the signal may affect the amount of energy delivered to the tissue. For instance, higher frequencies of alternating current (having shorter wavelengths) may deliver higher amounts of energy. Higher voltages and/or higher currents (the prospective amplitudes of an alternating current waveform) may deliver higher amounts of energy. The voltage and current may be related to each other according to Ohm's law (V=IR) depending on the resistivity of the treated tissue. In various implementations, the frequency and/or the voltage/current of the RF energy may be modulated to adjust the amount of power or energy delivered to the tissue. In some embodiments, the frequency may be adjustable between approximately 1 kHz and 100 MHz, between 100 kHz and 50 MHz, and/or between 0.5 MHz and 10 MHz. For example, a higher power level (e.g., level 10) may utilize a frequency of about 2 MHz and a lower power level (e.g., level 5) may use a frequency of about 1 MHz. Some levels may employ the same frequency but have varying amplitudes of voltage/current. In some embodiments, the processor may employ one or more algorithms for determining the appropriate frequency and voltage/current combination to deliver the desired amount of energy. For instance, in some implementations, increasing the energy through higher frequency or higher current/voltage may differentially affect the amount of pain perceived by the patient.

FIG. 3C schematically depicts an image of the display 124 in which a plurality of coagulation volumes 126 have been visually depicted on the ultrasound image. FIG. 3C also shows an image or depiction of the distal end of the handpiece 102 overlaid on the ultrasound image. In some embodiments, the display 124 may show or otherwise depict the relative positioning of the needle plate 114 having the microneedle array 110 or at least one or more of the microneedles 112 on the image of the tissue. The microneedles 112 may be shown over the skin surface and/or penetrating the tissue at any possible penetration depth achievable by the microneedling system 100. The size and/or shape of the volumes of coagulation may be predicted based on algorithms which may account for the operating parameters and/or the ultrasound assessment of the skin. The display may depict expected widths, volumes, temperatures, and/or separation distances of the volumes of coagulation 126. An operator may make further adjustments based on the expected characteristics of the volumes of coagulation 126. In some embodiments, a representative volume of coagulation (e.g., an average volume of coagulation) may be input by the operator and/or predetermined by a stored program. The needle penetration depth, the pulse duration, the frequency, and/or the power may be adjusted according to the representative volume of coagulation alone or in combination with other inputs determined by the ultrasound probe 120, as described elsewhere herein. As shown in FIG. 3C, the display 124 may depict the volumes of coagulation 126 at different depths according to the variable penetration depth of the microneedles 112. In some embodiments, the microneedling system 100 may penetrate the same area of interest repeatedly with microneedles 112 using different penetration depths to result in a three-dimensional array of volumes of coagulation 126 as shown in FIG. 3C. The remaining operating parameters may be the same or different for each penetration depth. In some embodiments, the microneedling system 100 may be configured to rapidly perform multiple penetrations at different depths before the operator substantially moves the handpiece 102 to a different area of skin. For instance, the motor 108 may cycle between two or more penetration depths in a regular pattern. In some embodiments, multiple passes may be made over the same treatment area with the penetration depth being different for each pass. The microneedling system 100 may modulate the penetration depth according to any of these protocols based on a preselected algorithm. The use of the ultrasound probe 120 to measure skin thickness and/or skin composition and optionally, the use of algorithms to adjust operating parameters, may advantageously reduce user error in operating a microneedling system. Accordingly, the incorporation of an interrogative modality such as ultrasound and optionally the automated adjustment of parameters based on the data collected, may reduce the amount of training and expertise required by an operator to effectively use the microneedling system 100.

Figure 4:
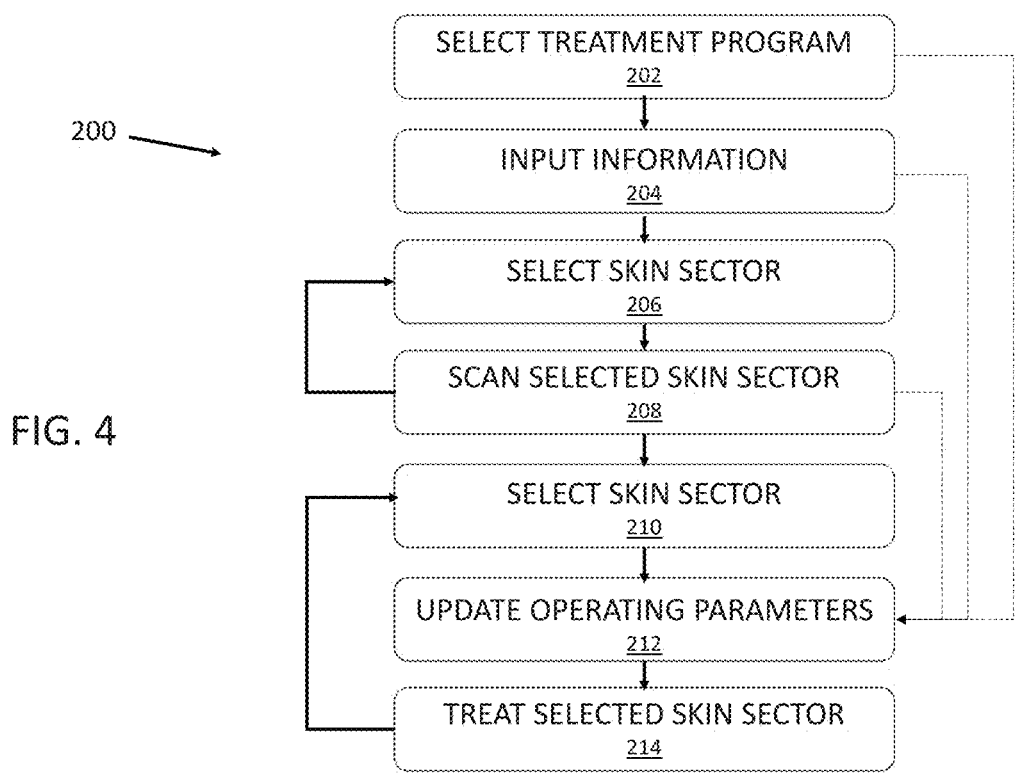
FIG. 4 schematically depicts the steps of an example procedure for using the microneedling system to treat the skin of a patient.

FIG. 4 schematically illustrates the steps of an example procedure 200 of using the microneedling system 100 to treat a patient. The procedure 200 depicted may be modified according to any of the steps disclosed elsewhere herein. The steps may be repeated as desired or where possible performed in different orders. Some of the steps may be optional. In some embodiments, the procedure 200 may involve a step 202 of user selecting a treatment program (e.g., via interface 122) for a treatment session. The program selection step 202 may be performed at the beginning of a treatment session or anywhere prior to a treatment step. The same program may be used for treating multiple areas or sectors of a patient's skin or a different program may be used for different sectors. For instance, the program may comprise algorithms for adjusting the operating parameters which are suited for specific conditions, such as treating acne scarring or tightening of the skin. In some implementations, the programs may be very specific, including different programs for treatment of fine lines, wrinkles, sun damage, stretch marks, pigmentation, pore size, skin texture, acne scarring, etc. The program may be designed as part of a specific treatment regimen comprising a plurality of planned treatment sessions. The program may be designed for one or more specific sectors of the skin. The program may be customized for patient characteristics, such as age and/or gender. The system 100 may be provided with a number of preset programs and/or users may manually enter or download/upload customized programs which are saved to memory for later use. In some of the embodiments, some of the operating parameters may be further adjustable (e.g., overridden) or optimizable after selection of a program. In some implementations, the procedure 200 may not use a program or the selection of a program may be optional. The system 100 may comprise default operating parameters that are used or adjusted by other means as described elsewhere herein.

The procedure 200 may involve a user input step 204 in which information such as operating parameters or other variables which may be considered by one or more algorithms for adjusting one or more operating parameters is input (e.g., via interface 122) by a user into the system 100. For instance, a user may input an operating parameter such as a power level, energy frequency, voltage/current level, pulse duration, and/or microneedle penetration depth. A user may input variables such as a total coagulation volume, patient age, patient body mass index (BMI), patient gender, etc. which may be input into an algorithm for adjusting an operating parameter. The user input step 204 may be performed at the beginning of a treatment session or anywhere prior to a treatment step. In some implementations, the input information may be changed or updated at any time. In some embodiments, a user may be queried by the system 100 for the input of information. In some embodiments, the information which a user is queried for or for which a user may enter may depend on the selection of a program in step 202. In some embodiments, the user input step 204 may replace the program selection step 202. The user input step 204 may be optional. In some implementations, the system 100 may be operated without any additional information being input by the user.

In some embodiments, the procedure 200 may involve the use of a non-invasive interrogative probe such as the ultrasound probe 120 to collect additional information about the patient skin. The information collected by the probe 120 may be correlated to specific regions or sectors of skin (e.g., the forehead, cheek, periorbital region, stomach, etc.) which are expected to be relatively homogeneous. Prior to collecting the information with the probe 120, a user may select (e.g., via interface 120) a sector from which the information is to be collected as depicted in step 206. The skin sector selection step 206 may involve the display of various sectors on the display 124 from which a user may select. The skin sector selection step 206 may allow the subsequent information collected by the probe 120 to be associated with a specific sector of skin such that the operating parameters may be adjusted differentially for different sectors, depending on the sector's specific properties, as described elsewhere herein. The available sectors of skin may be broadly defined (e.g., face) and/or narrowly defined (e.g., chin). In some embodiments, the user may define custom sectors. The sectors may be named, numbered, or otherwise identified such that the user may later recall the data from that specific sector. In some embodiments, the skin sector selection step 206 may be optional and the procedure 200 may assume all of the scanned skin for a particular treatment is substantially homogeneous, particularly if only a small area is to be treated.

In step 208, the probe 120 may be used to scan one or more areas of skin which are to be subsequently treated with the microneedling handpiece 102. For instance, the probe 120 may measure the thickness of one or more layers of skin such as the epidermis and dermis. The probe 120 may be placed into contact and/or placed substantially close to the surface of the patient's skin near an area to be treated and moved across the surface of skin for a sector. The probe 120 may be moved continuously across the skin (e.g., in a raster-like pattern). The probe 120 may be kept in substantially uniform contact pressure or a substantially uniform distance from the surface of the skin. In some implementations, the probe, e.g., a non-invasive probe, utilizes a pressure sensor to prevent the user from compressing the skin and/or altering the skin layer thickness when probing. An example of such an implementation is a non-invasive probe incorporating a LED light on the proximal end, where the LED light is configured to alert the user when the correct force is applied, or when too much and/or not enough force is applied, e.g., by changing color (green to red), or by flashing a signal (e.g., constant light for correct pressure, fast flashing for too much or no light for too little). The sensor and/or alert device (LED, speaker, haptics generator) can be incorporated into the sensing area of the probe or into a handpiece of the probe. Alternate alert features can also be incorporated, e.g., audio or haptics, that signal to the user when the correct force is applied, or when too much and/or too little force is applied. In some implementations, the probe 120 may be moved over the same area multiple times as the probe 120 interrogates the skin and collects information. In some implementations, a medium such as a gel (e.g., ultrasound gel) may be applied to the skin and the probe 120 may be placed into contact with the medium. The medium may provide lubrication for smoothly translating the probe 120 across the skin of the patient. The system 100 may display images of the skin and/or delineations and/or measurements of the skin on the display 124 in real time or another suitable mode as described elsewhere herein. The system 100 may perform any suitable aggregation of the collected data such as averaging the thicknesses over a sector of skin. In some embodiments, the system 100 may alert a user if measurements within a defined sector in which the skin is expected to be relatively homogenous vary by more than a predetermined threshold (e.g., 5%, 10%, 25%, 50%, 100%, 200%, 500% variation). The numerical measurements and/or graphical representations thereof may be displayed to a user on the display 104 in real time and/or after scanning of a sector is complete. In embodiments, in which the user selected a specific skin sector in step 206, the data may be associated in the memory of system 100 to that specific sector. After completion of a scanning step 208, the user may optionally return to step 208 and select or set another sector to be scanned before repeating the scanning step 208, for instance, if the treatment is to be performed over heterogeneous sectors of skin. The user may repeat these sequence of steps any desired number of times.

After the skin of the patient has been scanned or probed, the user may proceed to treat the skin using the microneedling handpiece 102. In some embodiments, the user may first select a skin sector to be treated. This skin selection step 210 may be used in instances in which the user scanned multiple sectors of skin in steps 206 and 208 in order to recall the appropriate probe 120 data for updating the operating parameters appropriately for treating a specific sector of skin. The selectable skin sectors may correspond to those from which a user was able to select or for which a user input a customized sector in step 206. In some embodiments, the skin sector selection step 210 may be optional, particularly where a user has not differentiated different sectors of skin prior to scanning with probe 120.

Prior to initiating the treatment of the skin, the operating parameters of the system 100 (e.g., the power level, energy frequency, voltage/current level, pulse duration, and/or microneedle penetration depth) may be adjusted based at least in part on the measurements obtained from probe 120. In step 212, the system 100 may update the operating parameters of the array 110 (e.g., the current/voltage level, pulse duration, microneedle penetration depth, etc.) as described elsewhere herein. The adjustment may be automatic and/or manual. In some embodiments, the system 100 may update the operating parameters based at least in part on an algorithm corresponding to a treatment program selected in step 202. In some embodiments, the system 100 may update the operating parameters based at least in part on user input information obtained in step 204. In implementations where a user selected/identified and scanned multiple sectors of skin in step 206 and then reselected the sector in step 210, the system 100 may specifically use the data obtained from the specifically selected sector of skin in step 208 to adjust the operating parameters according to predetermined algorithms. The dashed arrows indicate information which may be input into one or more algorithms by which a processor of the system 100 may update the operating parameters prior to initiating treatment of a skin sector in step 214, as described elsewhere herein. Once the operating parameters have been set, the user may proceed to treat skin of the desired or selected sector using the microneedling handpiece 102. In some embodiments, the operating parameters, previously obtained images of the skin sector being treated, and/or previously obtained measurements of the skin sector being treated may be displayed during the treatment step 214.

In some implementations, the user may repeat procedure 200 as desired over the same and/or different areas of the body. The user may use the same or different programs. The procedure 200 may be preceded and/or followed by pre-treatment or post-treatment processing, respectively, of the skin. For instance, prior to procedure 200 the skin may be cleaned and/or exfoliated. Subsequent to the treatment the skin, therapeutic agents may be applied to the skin such as platelet rich plasma (PRR). In some embodiments, the system 100 may store to memory a history of treatment parameters, including operating parameters, duration of treatment, total energy applied, skin sectors treated, etc., for a specific patient. The history may be recalled on subsequent treatment sessions to help advise a user on future appropriate treatments.

In some embodiments, a lubricant (e.g., an ultrasound gel) can advantageously be employed to facilitate movement of a non-invasive or imaging probe across the patient's skin. Such lubricants can include conventional ultrasound lubricants. Advantageously, the lubricant can include therapeutic agents or excipients such as those employed in topical therapeutic or cosmetic compositions. Such agents and excipients include but are not limited to protective agents, emollients, humectants, antibiotics, antifungals, antivirals, antiprotozoals, anti-acne agents, anesthetic agents, analgesic agents, steroidal anti-inflammatory agents, non-steroidal anti-inflammatory agents, antipruritics, antioxidants, antihistamines, a vitamin or vitamin complex, a hormone, an anti-wrinkle agent, an anti-skin atrophy agent, peptides or peptide derivatives, and combinations thereof.

Lubricants or gels, e.g., ultrasound gels, for topical use can be prepared using techniques as are known in the art. See, e.g., Handbook of Cosmetic Science and Technology, Fourth Edition, edited by André O. Barel, Marc Paye, Howard I. Maibach, CRC Press, 2014, the contents of which are hereby incorporated by reference in its entirety. Various formulations are possible, including both solid and liquid forms. For example, a clear gel stick composition can be prepared that contains 60 to about 90% of an aliphatic polyhydric alcohol (e.g., a $C_{2-6}$ alcohol containing from 2 to 6 hydroxyl groups); 1-10% of a thickener, such as a fatty acid salt; and 1-10% of a water-soluble emollient, e.g., a polyoxyalkylene ether of a $C_{8-22}$ fatty alcohol, along with other agents and excipients. For liquid formulations (e.g., gel or lubricant forms), a silicone, e.g., a cyclosiloxane or linear silicone (e.g., silicone elastomer), can be employed as a carrier. One type of carrier is a dimethicone crosspolymer gel, e.g., dimethicone crosspolymer in cyclopentasiloxane. Other dimethicone crosspolymers include cyclopentasiloxane, dimethicone/vinyldimethicone crosspolymer; dimethicone, dimethicone/vinyl dimethicone crosspolymer; and isodecane dimethicone/vinyl dimethicone crosspolymer. Aqueous gels can comprise a water-oil emulsion, e.g., an emulsion of s silicone component. Typically, the carrier is present in the lubricant an amount of from about 70 wt. % to about 99 wt. %, or about 80 wt. % to about 95 wt. %, or about 85 wt. % to about 90 wt. %, e.g., in a topical formulation for application to skin to lubricate passage of a probe across the skin.

Fatty acids and alcohols, or their derivatives, can be employed to enhance penetration of therapeutic agents. Examples include lecithin, phospholipids, squalane, methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acidpalmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., $C_6$-12 fatty acids, or the like. Typical amounts when employed in topical formulations suitable for use as lubricants are from 1% by weight to 4% by weight.

In some embodiments, the lubricating formulations can include components such as anti-inflammatory agents, antioxidants, solubility enhancers, a carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical lubricant use comprise a dermatologically acceptable vehicle. The vehicle may be aqueous or nonaqueous. The dermatologically acceptable vehicle may be in the form of a lotion, a gel, an ointment, a liquid, a cream, or an emulsion. If the vehicle is an emulsion, the emulsion may have a continuous aqueous phase and a discontinuous nonaqueous or oil phase (oil-inwater emulsion), or a continuous nonaqueous or oil phase and a discontinuous aqueous phase (water-in-oil emulsion). When applied topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) can be employed to assist in penetration of therapeutic agents into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers are also known as silicone elastomers. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a cross-linker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the lubricant formulations may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic formulation suitable for topical application include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, active ingredients may be dissolved or dispersed in a hydrophobic oil phase, and the oil phase may then be emulsified in an aqueous phase comprising water, alone or in combination with lower alcohols, glycerin, and/or glycols, or dissolved in the aqueous phase and emulsified in oil. It is generally preferred to employ anhydrous compositions, as the presence of water can result in stinging upon administration to skin tissues subjected to microneedling. Anhydrous formulations may also act to prevent the development of water-based irritant contact dermatitis in damaged or sensitive skin, which may produce rashes and skin irritation that may retard wound healing. However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Certain of the formulations as described herein can be advantageously employed where it is desirable to minimize osmotic shock.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, methylcellulose, and polyethoxylated alkane thiols. Other suitable thickening agents include, for example, xanthan gum, carboxymethyl cellulose, hydroxypropyl cellulose, carbomer, and the like. The concentration of the thickener can be adjusted depending upon the thickening agent selected. An amount is typically employed that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing active ingredients. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the active ingredients.

The topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8, so as to provide a formulation suitable for topical application. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The lubricating compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Additional agents having pharmacological activity can advantageously be employed in the lubricating compositions of the embodiments. Anti-infective agents include, but are not limited to, anthelmintics (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethasone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone. Other anti-inflammatory agents include glycyrrhizin, glycyrrhetinic acid, and pantothenic acid. Antihyperalgesic agents can also be included in the formulation. Hyperalgesia is a pain response to stimuli that are not normally painful, induced by the lowering of the nociceptor threshold level. Anti-hyperalgesic agents include compounds that act on GABA receptors (clobazam and clonazepam), N-methyl-D-aspartate (NMDA) receptor antagonists such as neramexane, gabapentin, buprenorphine, NSAIDs, glucocorticoids, pregabalin, and tramadol.

In certain embodiments, the addition of emollients, emulsion stabilizers, moisturizers, excipients, and other compounds may be modified to enhance the sensory properties of the lubricating compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others.

The lubricating formulation can further contain components as are employed in skin care formulations. For example, collagen and elastin formation and matrix agents such as hyaluronic acid, pentapeptides, tripeptides, and vitamin A palmitate can be included. Hyaluronic acid is naturally found as part of the connective tissue matrix layer of the dermis, along with the fibers collagen and elastin. Hyaluronic acid hydrates the skin, transports essential nutrients to the skin, and adds volume, thereby contributing to the skin's healthy appearance, such that it is often used in skin care products. Polypeptides, such as pentapeptides and tripeptides, or docrin or proteoglycan analogs, form part of the building blocks for restoring collagen and elastin fibers. Vitamin A palmitate (retinyl palmitate) is the ester of retinol (vitamin A) and palmitic acid. After absorption through the skin, retinyl palmitate is converted to retinol, and then to retinoic acid. Tretinoin (3,7,-dimethyl-9-(2,6,6-trimethyl-1-cyclohexenyl)-nona-2,4,6,8-tetraenoic acid) is the all-trans retinoic acid that is the active form of vitamin A and is a common component in skin care compositions.

Exemplary Methods and Systems

Method 1: A method of inducing collagen regeneration in the skin of a patient, the method comprising: measuring the thickness of at least one layer of the skin of the patient with a non-invasive probe; contacting the skin of the patient and delivering electrical energy to the skin of the patient via an electrode array; and adjusting via a processor, based on a measurement of the probe, one or more operating parameters of the electrode array selected from the group consisting of: a waveform frequency of the electrical energy, an amplitude of the waveform, a duration of the electrical energy deliver, and the depth of penetration into the skin of the at least one electrode.

Method 2: Method 1, wherein the probe is an ultrasound probe.

Method 3: Method 1, wherein the probe is a near-infrared probe.

Method 4: Any one of Methods 1 to 3, wherein the electrode array comprises a plurality of electrodes.

Method 5: Method 4, wherein the plurality of electrodes comprises electrodes of opposite polarity.

Method 6: Method 5, wherein one of the polarities is electrical ground.

Method 6: Any one of Methods 1 to 6, further comprising applying a ground electrode separate from the electrode array to the patient.

Method 8: Any one of Methods 1 to 5, wherein the electrode array comprises at least one microneedle electrode configured to be inserted the skin of the patient.

Method 9: Method 8, wherein the at least one microneedle is configured to be inserted into the skin at an adjustable penetration depth.

Method 10: Method 9, comprising adjusting the penetration depth in response to the measurement of the probe.

Method 11: Any one of Methods 7 to 10, wherein the microneedle electrode is configured to be inserted such that a distal tip of the microneedle electrode reaches the dermis.

Method 12: Any one of Methods 7 to 11, wherein the microneedle electrode is insulated.

Method 13: Any one of Methods 1 to 11, wherein the microneedle electrode is uninsulated.

Method 14: Any one of Methods 1 to 10, wherein the electrode array comprises a surface electrode configured to be pressed into contact with the surface of the skin without puncturing the skin.

Method 15: Method 14, wherein the surface electrode is a plate electrode.

Method 16: Any one of Methods 1 to 15, comprising adjusting, via the processor, the waveform frequency in response to the probe measurement.

Method 17: Any one of Methods 1 to 16, comprising adjusting, via the processor, the waveform amplitude in response to the probe measurement.

Method 18: Any one of Methods 1 to 17, comprising adjusting, via the processor, the pulse duration of the electrical energy in response to the probe measurement.

Method 19: Any one of Methods 1 to 18, comprising adjusting, via the processor, a power level of the electrode array by adjusting a combination of the waveform amplitude and waveform frequency.

Method 20: Any one of Methods 1 to 19, comprising adjusting, via the processor, the one or more operating parameters of the electrode array based in part on an input desired volume of coagulation.

Method 21: Any one of Methods 1 to 20, comprising estimating, via the processor, one or more volumes of coagulation based on the operating parameters and the probe measurement.

Method 22: Any one of Methods 1 to 21, further comprising displaying an image of the skin in which at least one layer of the skin is delineated from another.

Method 23: Method 22, comprising displaying the penetration depth of one or more microneedles on the image.

Method 24: Any one of Methods 22 or 23, comprising displaying one or more predicted volumes of coagulation on the image.

Method 25: Any one of Methods 22 to 24, comprising displaying one or more measurements of the thickness of a layer of the skin.

Method 26: Any one of Methods 1 to 25, comprising aggregating measurements from the probe, via the processor, to determine a representative measurement for a sector of skin.

Method 27: Any one of Methods 1 to 25, comprising adjusting the operating parameters of the electrode array based on a selection of a specific sector of skin which is to be treated.

Method 28: Method 27, wherein the selectable sectors comprises the face.

Method 29: Any one of Methods 27 or 28, wherein the selectable sectors comprise different sectors of the face.

Method 30: Any one of Methods 1 to 29, comprising, via the processor, delineating the epidermis, dermis, and subcutaneous tissue of the skin of the patient.

Method 31: Any one of Methods 1 to 30, further comprising inputting operating parameters into a user interface.

Method 32: Any one of Methods 1 to 31, further comprising selecting one of a plurality of user-selectable programs stored on a memory to adjust the operating parameters of the electrode array in response to the probe measurement.

Method 33: Method 32, wherein at least one of the user-selectable programs is specific to a skin condition to be treated.

Method 34: Any one of Methods 1 to 33, wherein the probe is disposed on the handpiece.

Method 35: Method 34, wherein the probe is positioned laterally to the electrode array.

Method 36: Method 34, wherein the probe is axially aligned with the electrode array relative to a longitudinal axis extending from the proximal end to the distal end of the handpiece.

Method 37: Method 36, wherein the probe is positioned proximally behind the electrode array.

Method 38: Any one of Methods 1 to 33, wherein the probe is disposed on an instrument separate from the handpiece.

Method 39: Method 38, wherein the instrument and the handpiece are operatively coupled to a single housing unit for modulating operation of both the probe and the electrode array.

Method 40: Any one of Methods 1 to 39, wherein the electrode array is detachable from the handpiece.

Method 41: Any one of Methods 1 to 40, wherein the electrode array is configured to deliver the electrical energy in one or more confined electrocoagulation volumes.

Method 42: Method 41, wherein the one or more electrocoagulation volumes are defined by a threshold temperature.

Method 43: Method 42, wherein the threshold temperature is about 55 degrees Celsius.

Method 44: Any one of Methods 41 to 43, further comprising estimating the size of the one or more electrocoagulation volumes.

Method 45: Method 44, wherein the estimating is based on one or more of the power level, frequency, pulse duration, and/or total treatment time.

Method 46: Any one of Methods 44 or 45, further comprising automatically adjusting the depth of the one or more electrocoagulation volumes based on the estimated size of the one or more electrocoagulation volumes and based on a measured thickness of the at least one layer of skin as measured by the non-invasive probe.

Method 47: Method 46, wherein the depth of the one or more electrocoagulation volumes is adjusted by automatically adjusting the penetration depth of the at least one electrode.

Method 48: Any one of Methods 46 or 47, wherein the depth of the one or more coagulation volumes is adjusted in order to confine the one or more coagulation volumes to a selected layer of skin.

Method 49: Method 48, wherein the selected layer is the dermis.

Method 50: Any one of Methods 1 to 29, further comprising minimizing the penetration depth of the at least one electrode.

Method 51: Any one of Methods 41 to 50, further comprising maximizing the size of the one or more coagulation volumes for a selected depth while preventing the one or more coagulation volumes from extending into one or more select layers of skin.

System 52: A system for inducing collagen regeneration in the skin of a patient, the system comprising: a handpiece having a proximal end and a distal end, the distal end comprising an electrode array, the electrode array comprising at least one electrode for delivering energy to the skin of the patient; a non-invasive probe configured to delineate and measure the thickness of at least one layer of the skin of the patient; a processor operatively coupled to the electrode array and operatively coupled to the probe, wherein in response to a measurement of the probe the processor is configured to adjust one or more operating parameters of the electrode array selected from the group consisting of a waveform frequency of the energy, an amplitude of the waveform, a duration of the energy deliver, and the depth of penetration into the skin of the at least one electrode; and memory storing instructions for operating the processor.

System 53: System 52, wherein the probe is an ultrasound probe.

System 54: System 52, wherein the probe is a near-infrared probe.

System 55: System 52, wherein the probe is a confocal laser scanning microscopy probe.

System 56: System 52, wherein the probe is an optical coherence tomography probe.

System 57: System 52, wherein the probe is a diffuse reflectance spectroscopy probe.

System 58: System 52, wherein the probe is a computerized tomography probe.

System 59: System 52, wherein the probe is a magnetic resonance imaging probe.

System 60: System 52, wherein the probe is an atomic force microscopy probe.

System 61: System 52, wherein the probe is a positron emission tomography probe.

System 62: System 52, wherein the probe is an ultrasound elastography probe.

System 63: System 52, wherein the probe is a photoacoustic imaging probe.

System 64: System 52, wherein the probe is a magnetic particle imaging probe.

System 65: System 52, wherein the probe is an electrical impedance tomography probe.

System 66: System 52, wherein the probe is a Doppler ultrasonography probe.

System 67: Any one of Systems 52 to 66, wherein the electrode array comprises a plurality of electrodes.

System 68: System 67, wherein the plurality of electrodes comprises electrodes of opposite polarity.

System 69: System 68, wherein one of the polarities is electrical ground.

System 70: Any one of Systems 52 to 69, further comprising a ground electrode separate from the electrode array, the ground electrode configured to be coupled to the patient.

System 71: Any one of Systems 52 to 70, wherein the electrode array comprises at least one microneedle electrode configured to be inserted the skin of the patient.

System 72: System 71, wherein the at least one microneedle is configured to be inserted into the skin at an adjustable penetration depth.

System 73: System 72, wherein the penetration depth is adjusted in response to the measurement of the probe.

System 74: Any one of Systems 71 to 73, wherein the microneedle electrode is configured to be inserted such that a distal tip of the microneedle electrode reaches the dermis.

System 75: Any one of Systems 71 to 74, wherein a portion of the microneedle electrode is insulated, such that an area of non-insulated microneedle electrode is defined to produce an electrocoagulation.

System 76: Any one of Systems 71 to 75, wherein the microneedle electrode is uninsulated.

System 77: Any one of Systems 52 to 76, wherein the electrode array comprises a surface electrode configured to be pressed into contact with the surface of the skin without puncturing the skin.

System 78: System 77, wherein the surface electrode is a plate electrode.

System 79: Any one of Systems 52 to 78, wherein the processor is configured to adjust the waveform frequency in response to the probe measurement.

System 80: Any one of Systems 52 to 79, wherein the processor is configured to adjust the waveform amplitude in response to the probe measurement.

System 81: Any one of Systems 52 to 80, wherein the processor is configured to adjust the pulse duration of the electrical energy in response to the probe measurement.

System 82: Any one of Systems 52 to 81, wherein the processor is configured to adjust a power level of electrode array by adjusting a combination of the waveform amplitude and waveform frequency.

System 83: Any one of Systems 52 to 82, wherein the processor is configured to adjust the one or more operating parameters of the electrode array based in part on an input desired volume of coagulation.

System 84: Any one of Systems 52 to 83, wherein the processor is configured to estimate one or more volumes of coagulation based on the operating parameters and the probe measurement.

System 85: Any one of Systems 52 to 84, further comprising a display operatively coupled to the processor, the display configured to depict an image of the skin in which at least one layer of the skin is delineated from another.

System 86: System 85, in which the processor is configured to depict the penetration depth of one or more microneedles on the image.

System 87: Any one of Systems 85 or 86, in which the processor is configured to depict one or more predicted volumes of coagulation on the image.

System 88: Any one of Systems 85 to 87, in which the processor is configured to depict one or more measurements of the thickness of a layer of the skin on the display.

System 89: Any one of Systems 52 to 88, in which the processor is configured to aggregate measurements from the probe to determine a representative measurement for a sector of skin.

System 90: Any one of Systems 52 to 89, in which the processor is configured to adjust the operating parameters of the electrode array based on a selection of a specific sector of skin which is to be treated.

System 91: System 90, wherein the selectable sectors comprises the face.

System 92: Any one of Systems 90 or 91, wherein the selectable sectors comprise different sectors of the face.

System 93: System 90, wherein the selectable sectors comprises a preselected region of the body.

System 94: Any one of Systems 90 or 91, wherein the selectable sectors comprise different sectors of the preselected region of the body.

System 95: Any one of Systems 52 to 94, wherein the processor is configured to delineate the epidermis, dermis, subcutaneous tissue, and muscle.

System 96: Any one of Systems 52 to 95, further comprising a user interface through which a user can adjust the operating parameters and/or input parameters.

System 97: Any one of Systems 52 to 96, wherein the memory stores a plurality of user-selectable programs which use different algorithms for adjusting the operating parameters of the electrode array in response to the probe measurement.

System 98: System 97, wherein at least one of the user-selectable programs is specific to a skin condition to be treated.

System 99: Any one of Systems 52 to 98, wherein the probe is disposed on the handpiece.

System 100: System 99, wherein the probe is positioned laterally to the electrode array.

System 101: System 99, wherein the probe is axially aligned with the electrode array relative to a longitudinal axis extending from the proximal end to the distal end of the handpiece.

System 102: System 101, wherein the probe is positioned proximally behind the electrode array.

System 103: Any one of Systems 52 to 102, wherein the probe is disposed on an instrument separate from the handpiece.

System 104: System 103, wherein the instrument and the handpiece are operatively coupled to a single housing unit for modulating operation of both the probe and the electrode array.

System 105: Any one of Systems 52 to 104, wherein the electrode array is detachable from the handpiece.

System 106: Any one of Systems 52 to 105, wherein the electrode array is configured to deliver the electrical energy in one or more confined damage volumes.

System 107: System 106, wherein the one or more damage volumes are defined by a threshold temperature.

System 108: System 107, wherein the threshold temperature is about 55 degrees Celsius.

System 109: System 106, wherein the one or more damage volumes are defined by a threshold electrical impedance input.

System 110: Any one of Systems 106 to 109, wherein the system is configured to estimate the size of the one or more damage volumes.

System 110: System 110, wherein the system is configured to estimate the size of the one or more damage volumes based on one or more of the power level, frequency, pulse duration, and/or total treatment time.

System 112: Any one of Systems 110 or 111, wherein the system is configured to automatically adjust the depth of the one or more damage volumes based on the estimated size of the one or more damage volumes and based on a measured thickness of the at least one layer of skin as measured by the non-invasive probe.

System 113: System 112, wherein the depth of the one or more damage volumes is adjusted by automatically adjusting the penetration depth of the at least one electrode.

System 114: Any one of Systems 112 or 113, wherein the depth of the one or more damage volumes is adjusted in order to confine the one or more damage volumes to a selected layer or layers of skin.

System 115: System 112, wherein one or more damage volumes is adjusted by automatically adjusting waveform amplitude or period.

System 116: System 115, wherein the adjustment of the waveform amplitude or period is adjusted by accounting for an electrical impedance of the selected layer or layers of skin.

System 117: System 116, wherein the selected layer is the dermis.

System 118: Any one of Systems 52 to 117, wherein the system is configured to minimize the penetration depth of the at least one electrode.

System 119: Any one of Systems 52 to 118, wherein the system is configured to maximize the size of the one or more damage volumes for a selected depth while preventing the one or more damage volumes from extending into one or more select layers of skin.

System 120: Any one of Systems 52 to 119, wherein the electrode array comprises a plurality of electrodes, the system further comprising an ultrasonic array disposed within the distal end of the handpiece, wherein the ultrasonic array comprises a plurality of ultrasound integrated circuits, wherein each ultrasound integrated circuit is situated between at least two electrodes.

System 121: System 120, wherein each of the ultrasound integrated circuits are Micro-Electro-Mechanical Systems (MEMS) transducers.

System 122: System 121, wherein the Micro-Electro-Mechanical Systems (MEMS) transducers are selected from the group consisting of piezoelectric MicroMachined Ultrasound Transducers (pMUTs) and capacitive MicroMachined Ultrasound Transducers (cMUTs).

System 123: A system for inducing collagen regeneration in the skin of a patient, the system comprising: a handpiece having a proximal end and a distal end, the distal end comprising an electrode array comprising bipolar electrodes for producing a confined volume of electrocoagulation at a select depth beneath a surface of the skin of the patient; a non-invasive probe configured to delineate and measure the thickness of at least one layer of the skin of the patient; a non-invasive or invasive electrode configured to obtain electrical impedance values of at least one layer of the skin of the patient; and a processor operatively coupled to the electrode array and operatively coupled to the probe, wherein the processor is configured to adjust the depth of the volume of electrocoagulation beneath the surface of the skin according to an algorithm based in part upon a measurement of the non-invasive probe.

System 124: System 123, wherein the bipolar electrodes comprise a first electrode adapted to operate at a higher potential than a second electrode.

System 125: System 124, wherein the first electrode is adapted to operate at a positive potential and the second electrode is adapted to operate at a negative potential.

System 126: A system for inducing collagen regeneration in the skin of a patient, the system comprising: a handpiece having a proximal end and a distal end, the distal end comprising an electrode array comprising bipolar electrodes for producing a confined volume of electrocoagulation at a select depth beneath a surface of the skin of the patient; a non-invasive probe configured to delineate and measure the thickness of at least one layer of the skin of the patient; and a processor operatively coupled to the electrode array and operatively coupled to the probe, wherein the processor is configured to adjust the depth of the volume of electrocoagulation beneath the surface of the skin according to an algorithm based in part upon a measurement of the non-invasive probe.

Method 127: A method for inducing collagen regeneration in the skin of a patient, the method comprising: measuring the thickness of at least one layer of the skin of the patient with a non-invasive probe; producing a confined volume of electrocoagulation at a select depth beneath a surface of the skin of the patient; and adjusting via a processor the depth of the volume of electrocoagulation beneath the surface of the skin according to an algorithm based in part upon a measurement of the non-invasive probe.

Method 128: Method 127, wherein the volume of electrocoagulation corresponds to an amount of tissue damage produced by application of the method.

Method 129: Method 127, wherein the volume of electrocoagulation is predetermined by on demand fedback by optical modality.

Method 130: Method 127, wherein the volume of electrocoagulation is predetermined by on demand fedback by ultrasound.

Method 131: Method 127, wherein the volume of electrocoagulation is defined by an algorithm based on a frequency waveform amplitude and a treatment time of applied energy.

Method 132: Method 131, wherein the volume of electrocoagulation is further defined by a depth of penetration of an electrode.

Method 133: Method 131, wherein the volume of electrocoagulation is further defined by a bioimpedance of a skin layer.

Method 134: Any one of Methods 127 to 133, further comprising applying a lubricating formulation to the skin of the patient.

Method 135: Method 134, wherein the lubricating formulation comprises an active ingredient comprising an analgesic agent, an anti-hyperalgesic agent, and/or an anti-inflammatory agent.

Method 136: Method 134, wherein the lubricating formulation is applied prior to employing a probe.

Method 137: Method 134, wherein the lubricating formulation is applied prior to applying an energy modality tissue of the patient.

System 138: A system for inducing collagen regeneration in the skin of a patient, the system comprising: a handpiece having a proximal end and a distal end, the distal end comprising an electrode array and a noninvasive probe, the electrode array comprising a plurality of electrodes for delivering energy to the skin of the patient, the noninvasive probe comprising an ultrasonic array configured to delineate and measure the thickness of at least one layer of the skin of the patient, wherein the ultrasonic array comprises a plurality of ultrasound integrated circuits, wherein each ultrasound integrated circuit is situated between at least two electrodes of the electrode array; a processor operatively coupled to the electrode array and operatively coupled to the noninvasive probe, wherein in response to a measurement of the noninvasive probe the processor is configured to adjust one or more operating parameters of the electrode array selected from the group consisting of a waveform frequency of the energy, an amplitude of the waveform, a duration of the energy deliver, a depth of penetration into the skin of each of the electrodes, and a positioning of each of the electrodes; and memory storing instructions for operating the processor.

System 139: System 138, wherein each of the ultrasound integrated circuits are Micro-Electro-Mechanical Systems (MEMS) transducers.

System 140: System 139, wherein the Micro-Electro-Mechanical Systems (MEMS) transducers are selected from the group consisting of piezoelectric MicroMachined Ultrasound Transducers (pMUTs) and capacitive MicroMachined Ultrasound Transducers (cMUTs).

System 141: System 138, wherein each of the electrodes is a microneedle, and wherein the noninvasive probe is adapted to assess skin layer depth and microneedle positioning.

System 142: System 141, adapted to provide feedback of microneedle positioning.

System 145: System 141, adapted to assess electrocoagulation area and/or volume, and to automatically cease electrocoagulation once a precise volume of electrocoagulation has been achieved.

Any of the features of an exemplary system may be applicable to other aspects and embodiments identified herein. Moreover, any of the features of an exemplary system or method may be independently combinable, partly or wholly with other embodiments or features described herein in any way, e.g., one, two, or three or more embodiments or features may be combinable in whole or in part. Further, any of the features of an exemplary method or system may be made optional to other methods or systems. Any aspect or embodiment of an exemplary method may be performed by a system or apparatus of another aspect or embodiment, and any aspect or embodiment of a exemplary system or apparatus may be configured or adapted to perform a method of another aspect or embodiment.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Where a range of values is provided, it is understood that the upper and lower limit, and each intervening value between the upper and lower limit of the range is encompassed within the embodiments.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and suboperations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above with respect to components, elements, devices, modules, and circuitry, etc., including variations thereof, may be applied to the various operations described in connection with methods described herein, and vice versa, without departing from the scope of the present disclosure.

All numbers expressing quantities used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for inducing collagen regeneration in the skin of a patient, the system comprising:
    a handpiece having a proximal end and a distal end, the distal end comprising an electrode array and a noninvasive probe, the electrode array comprising a plurality of electrodes for delivering energy to the skin of the patient, the noninvasive probe comprising an ultrasonic array configured to delineate and measure the thickness of at least one layer of the skin of the patient, wherein the ultrasonic array comprises a plurality of ultrasound integrated circuits, wherein each ultrasound integrated circuit is situated between at least two electrodes of the electrode array;

a processor operatively coupled to the electrode array and operatively coupled to the noninvasive probe, wherein in response to a measurement of the noninvasive probe the processor is configured to adjust one or more operating parameters of the electrode array selected from the group consisting of a waveform frequency of the energy, an amplitude of the waveform, a duration of the energy deliver, a depth of penetration into the skin of each of the electrodes, and a positioning of each of the electrodes; and memory storing instructions for operating the processor.

2. The system of claim 1, wherein each of the ultrasound integrated circuits are Micro-Electro-Mechanical Systems (MEMS) transducers.

3. The system of claim 2, wherein the Micro-Electro-Mechanical Systems (MEMS) transducers are selected from the group consisting of piezoelectric MicroMachined Ultrasound Transducers (pMUTs) and capacitive MicroMachined Ultrasound Transducers (cMUTs).

4. The system of claim 1, wherein each of the electrodes is a microneedle, and wherein the noninvasive probe is adapted to assess skin layer depth and microneedle positioning.

5. The system of claim 4, wherein a portion of the microneedle electrode is insulated, such that an area of non-insulated microneedle electrode is defined to produce an electrocogulation.

6. The system of claim 5, wherein penetration depth is configured to be adjusted in response to the non-invasive probe measurement.

7. The system of claim 4, adapted to provide feedback of microneedle positioning.

8. The system of claim 4, adapted to assess electrocoagulation area and/or volume, and to automatically cease electrocoagulation once a precise volume of electrocoagulation has been achieved.

9. The system of claim 1, wherein the noninvasive probe is selected from the group consisting of an ultrasound probe, near-infrared probe, confocal laser scanning microscopy probe, optical coherence tomography probe, diffuse reflectance spectroscopy probe, computerized tomography probe, magnetic resonance imaging probe, atomic force microscopy probe, positron emission tomography probe, ultrasound elastography probe, photoacoustic imaging probe, electrical impedance tomography probe, and Doppler ultrasonography probe.

10. The system of claim 1, wherein the electrode array comprises a plurality of electrodes.

11. The system of claim 10, wherein the plurality of electrodes comprises electrodes of opposite polarity.

12. The system of claim 1, further comprising a ground electrode separate from the electrode array, the ground electrode configured to be coupled to the patient.

13. The system of claim 1, wherein the processor is configured to adjust the waveform frequency or waveform amplitude in response to the non-invasive probe measurement.

14. The system of claim 1, further comprising a display operatively coupled to the processor, the display configured to depict an image of the skin in which at least one layer of skin is delineated from another.

15. The system of claim 14, wherein the processor is configured to depict one or more measurements of the thickness of a layer of the skin on the display.

16. The system of claim 1, in which the processor is configured to aggregate measurements from the non-invasive probe to determine a representative measurement for a sector of skin.

17. The system of claim 1, in which the processor is configured to adjust the operating parameters of the electrode array based on a selection of a specific sector of skin which is to be treated.

18. The system of claim 1, further comprising a user interface through which a user can adjust the operating parameters and/or input parameters.

19. The system of claim 1, wherein the memory stores a plurality of user-selectable programs which use different algorithms for adjusting the operating parameters of the electrode array in response to the non-invasive probe measurement.

20. The system of claim 1, wherein the system is configured to maximize the size of one or more damage volumes for a selected depth while preventing the one or more damage volumes from extending into one or more select layers of skin.

* * * * *